United States Patent
Isshiki et al.

(10) Patent No.: US 10,370,729 B2
(45) Date of Patent: Aug. 6, 2019

(54) METHOD FOR DETECTING FUNGI, REACTION SOLUTION FOR PCR, AND CARRIER FOR DETECTING FUNGI

(71) Applicant: Toyo Seikan Group Holdings, Ltd., Shinagawa-ku (JP)

(72) Inventors: Atsunori Isshiki, Tokyo (JP); Suguru Tanabe, Tokyo (JP); Hitoshi Takeharu, Tokyo (JP); Mami Kokaji, Tokyo (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 608 days.

(21) Appl. No.: 14/098,260

(22) Filed: Dec. 5, 2013

(65) Prior Publication Data
US 2014/0141993 A1 May 22, 2014

Related U.S. Application Data

(63) Continuation of application No. PCT/JP2012/001991, filed on Mar. 22, 2012.

(30) Foreign Application Priority Data
Jun. 9, 2011 (JP) .................................. 2011-129632

(51) Int. Cl.
C12Q 1/68 (2018.01)
C12Q 1/6895 (2018.01)
C12Q 1/686 (2018.01)

(52) U.S. Cl.
CPC ........... *C12Q 1/6895* (2013.01); *C12Q 1/686* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 8,975,489 | B2 * | 3/2015 | Craven | A01N 63/04 435/161 |
| 2008/0286792 | A1 | 11/2008 | Tomatsu et al. | |
| 2008/0299572 | A1 | 12/2008 | Tomatsu et al. | |
| 2010/0311040 | A1 | 12/2010 | Rodrigues Carvalho et al. | |
| 2011/0136117 | A1 | 6/2011 | Hosoya et al. | |

FOREIGN PATENT DOCUMENTS

| | | | |
|---|---|---|---|
| CN | 1587418 | A | 3/2005 |
| JP | 2007195454 | A | 8/2007 |
| JP | 2007202462 | A | 8/2007 |
| JP | 2008005760 | A | 1/2008 |
| JP | 2008035773 | A | 2/2008 |
| JP | 2008278848 | A | 11/2008 |
| JP | 2008278861 | A | 11/2008 |
| JP | 2009171986 | A | 8/2009 |
| JP | 2009284832 | A | 12/2009 |
| JP | 2010004879 | A | 1/2010 |
| JP | 2010115122 | A | 5/2010 |
| JP | WO 2010055868 | A * | 5/2010 ............... C12Q 1/68 |
| JP | 2010130915 | A | 6/2010 |
| JP | 2011155912 | A | 8/2011 |
| WO | 02079469 | A1 | 10/2002 |
| WO | 2006123295 | A2 | 11/2006 |
| WO | 2008/003244 | A1 | 1/2008 |

OTHER PUBLICATIONS

Yi Mattila et al. (Intl Journal of Food Microbiol, 2004, vol. 95, p. 267-285).*
Lowe et al. (Nucleic Acids Research, 1990, 18(7):1757-1761).*
McCartney et al. (Pest Manag Sci, 2003, 59:129-142).*
Lau et al. (J Clin Microbiol, 2008, 46(9):3021-3027).*
Huang et al. (J Clin Microbiol. 2006, 44(9):3299-3305) (Year: 2006).*
Bilodeau et al., Phytopathology, 2007, 97(5), p. 632-634.*
Written Opinion of the Internatioanl Search Authority issued in PCT/JP2012/001991 dated May 29, 2012 (10 pages).
Prodi, A. et al. 'Phialophora-Like Fungi Associated With Kiwifruit Elephantiasis.' Journal of Plant Pathology, 2008, vol. 90, No. 3, p. 487-494 (8 pages).
Whitelaw-Weckert, M.A. et al. 'Phylogenetic relationships and pathogenicity of Colletotrichum acutatum isolates from grape in subtropical Australia.' Plant Pathology, 2007, vol. 56, p. 448-463 (16 pages).
Aroca A. et al. 'PCR-Based Strategy To Detect and Identify Species of *phaeoacremonium* Causing Grapevine Diseases.' Applied Environmental Microbiology, May 2007, vol. 73, No. 9, p. 2911-2918 (8 pages).
Takeuchi Y. et al. 'Diagnosis and quatification of the pine wood nematode, *Bursaphelenchus xylophilus* (Steiner & Buhner), in wood of Pinus thunbergii with real-time PCR.' Nematological Research, Jun. 2009, vol. 39, No. 1, p. 9-16 (8 pages).
Glass N. L. et al. 'Develpment of Primer Sets Designed for Use with the PCR To Amplify Conserved Genes from Filamentous Ascomycetes.' Applied Enviromental Microbiology, Apr. 1995, vol. 61, No. 4, p. 1323-1330 (8 pages).
Lau A. et al. 'Multiplex Tandem PCR: a Novel Platform for Rapid Detection and Identification of Fungal Pathogens from Blood Culture Speciments.' Journal of Clinical Microbiology, Sep. 2008, vol. 46, No. 9, p. 3021-3027 (7 pages).

(Continued)

*Primary Examiner* — Stephanie K Mummert
(74) *Attorney, Agent, or Firm* — Osha Liang LLP

(57) ABSTRACT

A method for detecting fungi includes amplifying DNA fragments containing target regions in fungal DNA to confirm the presence or absence of an amplified product. As the target regions, both of the ITS region and the β-tubulin gene are used, and by using a primer set for amplifying the β-tubulin gene and a primer set for amplifying the ITS region in a reaction solution for PCR for amplifying the target regions, both of the target regions are simultaneously amplified according to one or two or more types of fungi.

4 Claims, 25 Drawing Sheets

Specification includes a Sequence Listing.

(56) References Cited

OTHER PUBLICATIONS

Wang L. et al. 'Fungal pathogenic nucleic acid detection achieved with a microfluidic microarray device.' Analytica Chimica Acta., 2008, vol. 610, p. 97-104 (8 pages).
Koch C. A. et al. 'Evaluation of thin films of agarose on glass for hybridization of DNA to identify plant pathogens with microarray technology.' Analytical Biochemistry, 2005, vol. 342, p. 93-102 (10 pages).
Yan L. et al. 'Development of a real-time PCR assay for the detection of Cladosporium fulvum in tomato leaves.' Journal of Applied Microbiology, 2008, vol. 104, p. 1417-1424 (8 pages).
Taisuke Kasetani et al., "Bunkazai o Rekka saseru Shinkin no Kenshutsu ~ Shikibetsu-yo DNA Micro Array 2-Aspergillus penicillioides Spegazzini no Shunai Keito-", Dai 37 Kai Kenji Taikai Yoshishu, The Society for Antibacterial and Antifungal Agents, Japan, Sep. 27, 2010, p. 224 (2PP-26) (2 page).
Hiroshi Takeharu et al., "Kabi Kensa ni Okeru DNA Micro Array no Yukosei", Dai 37 Kai Kenji Taikai Yoshishu, The Society for Antibacterial and Antifungal Agents, Japan, Sep. 27, 2010, p. 219 (2PP-21) (2 page).
Mami Kokaji et al., "DNA Micro Array Kabi Kensa ni Okeru Saiteki Baiyo Joken no Kento", Dai 37 Kai Kenji Taikai Yoshishu, The Society for Antibacterial and Antifungal Agents, Japan, Sep. 27, 2010, p. 207 (2PP-09) (2 page).
Fuyuki Aoyama, "Development of the rapid identification method using DNA array for fruit and fruit juice harmful Fungi", Kaji Kyokaiho, Japan Fruit Juice Associateion, Nov. 25, 2010, pp. 1 to 11 (11 pages).
International Preliminary Report on Patentability issued in PCT/JP2012/001991 dated Dec. 27, 2013 (2 pages).
International Search Report in corresponding International application No. PCT/JP2012/001991 dated May 29, 2012 (5 pages).
Office Action issued in corresponding Japanese Application No. 2011-068332 dated Apr. 21, 2015 (3 pages).
European Search Report issued in European Application no. 12796704.0 dated Oct. 24, 2014 (7 pages).
Office Action in corresponding Chinese Application No. 201280028342.3 dated Aug. 26, 2014 (12 pages).
EPO Communication pursuant to Article 94(3) EPC (Office Action) dated Feb. 20, 2018, issued by the European Patent Office in related European Patent Application No. 12 796 704.0 (5 pages).

\* cited by examiner

FIG. 2

| Primer | F/R | Sequence No. | Base sequence (5'→3') |
|---|---|---|---|
| For amplifying ITS region | F | 1 | TTGGTTCATTTAGAGGAAGTAAAAGTC |
| | R | 2 | CTGCCGTTCTTCATCGATGC |
| For amplifying β-tublin gene | F | 3 | GGTAACCAAATGGTGCTGCTTTC |
| | R | 4 | ACCCTCAGTGTAGTGACCCTTGGC |
| For amplifying Cladosporium sp. | F | 5 | AAGTGAACTTTCAGGCACCCG |

FIG. 3

| | Fungi to be detected | Sequence No. | ITS (5'→3') | Sequence No. | β-tubulin gene (5'→3') |
|---|---|---|---|---|---|
| (1) | Eurotium sp. | 6 | GTCTGAGTTTTTAGTTAAACAAT | 8 | AGGCCTCCAACAACAAATATGTC |
| | | 7 | GAAGACTAACATTTGAACAC | | |
| (2) | Aspergillus penicillioides | 9 | GAGACCTCAACCATGAACACT | 12 | CATCGTCAGCATGTCACACCGC |
| | | 10 | GAGACCTCAACCATTGAACACT | | |
| | | 11 | GAGACCTCTCAACCATTGAACA | | |
| (3) | Aspergillus vitricola | 13 | CTGAGTTTTCATAAAAGAAAAATCG | 15 | CCAAAGTCCAATTGGCATCAAACT |
| | | 14 | CTGAGTTTTCATAAAGAAAAATTG | | |
| (4) | Aspergillus Section Restricti | 16 | GAGTTTTCATATAAGAAAAATCG | 21 | ATCAATTAGTATGCCACGCAC |
| | | 17 | TTGCCGTCTGAGTTGTCATATACGAAA | | |
| | | 18 | CCGGAGACTCCAACATTGAACA | | |
| | | 19 | GTCTGAGTTTTCATATACGAAAAT | | |
| | | 20 | CTGAGTTTTCATATACGAAAAAT | | |
| (5) | Aspergillus Section Nidulantes | 22 | ACTACTGAACTTCATGCCTGAGAGT | 23 | TTTGATCGAGTCTTGGACGGGT |
| | | | | 25 | AACATCTCAGATCTGACTCG |
| (6) | Aspergillus Section Fumigati | 24 | GAACGCTGTTCTGAAAGTAT | 27 | TGAAAACGCTTTGCAACTCC |
| (7) | Aspergillus Section Flavi | 26 | GCAACTAAGGTACJAGTAAACA | 30 | TGTCAATTGATACCCAACGCG |
| (8) | Penicillium sp. | 28 | AGTCTGAGTGAAAATATAAATTATTTA | 31 | GATCTTTCAGGATTTGCAGC |
| | | 29 | TTGCAGTCTGAGCGAAAACGCA | 32 | GTATAAAGGCTTCTCTAATGTT |
| (9) | Stachybotrys chartarum | 33 | ACCCCAAACTCTTGTGTTTTTTCAG | 34 | CTCGGCTCACAATTTCCCA |
| (10) | Fusarium solani | 35 | CTGAGTAAAACAAGCAAATAAAT | 36 | TAGATTTGGTATAGGCTTGGG |
| (11) | Cladosporium sp. | 37 | ACTCTTGCGTAACTTTGCAGTCT | 38 | GGTGTTGTCAGTGTGTGGACGTGGA |
| | | | | 39 | TGAGGCTCTTGGGACGTGCG |
| (12) | Common to fungi | 40 | GCATCGATGAAGAACGCAG | 41 | GAGCCCGGTACCATGACGC |

FIG. 4

| | Sample | Types of fungi included (judged according to the ITS region sequence analysis of separated fungi) |
|---|---|---|
| Test 1 | A | *Aspergillus penicillioides* |
| | | *Eurotium* sp. |
| | | *Cladosporium* sp. |
| | | *Penicillium* sp. |
| | B | *Aspergillus penicillioides* |
| | | *Aspergillus versicolor* |
| | | *Cladosporium cladosporioides* |
| | C | *Aspergillus niger* |
| | | *Aspergillus parasiticus* or *A. sojae* or *A. flavus* or *A. oryzae* |
| | | *Cladosporium cladosporioides* |
| | | *Penicillium* sp. |
| | D | *Aspergillus gracilis* or *Aspergillus* sp. |
| | | *Aspergillus vitricola* |
| | | *Aspergillus penicillioides* or *A. conicus* or *A. gracilis* |
| | | *Aspergillus conicus* or *A. reastrictus* or *A. caesiellus* |
| | E | *Penicillium* sp. |
| | | *Cladosporium cladosporioides* |
| | | *Aspergillus tubingensis* or *A. niger* or *A. awamori* |
| | | *Aspergillus gracilis* or *A. restrictus* or *A. caesiellus* |
| | F | *Aspergillus penicillioides* |
| | | *Leptosphaerulina chartarum* |
| Test 3 | | *Eurotium* sp. |
| | G | *Aspergillus penicillioides* or *A. restrictus* |
| | | *Cladosporium cladosporioides* |
| | | *Acremonium* sp. |
| | | *Ascomycete* sp. or *Fusarium* sp. |
| | H | *Eurotium* sp. |
| | | *Cladosporium cladosporioides* |
| | | *Aspergillus penicillioides* |

FIG. 19

|  |  | Reference Example1 | Reference Example2 | Example 1 | Example 2 | Example 3 | Example 4 | Example 5 | Example 6 | Example 7 | Example 8 | Example 9 | Example 10 | Reference Example3 | Reference Example4 | Reference Example5 | Reference Example6 |
|---|---|---|---|---|---|---|---|---|---|---|---|---|---|---|---|---|---|
| Composition of culture medium | Water activity value | >0.95 | >0.98 | >0.95 | >0.98 | 0.975 | >0.98 | >0.98 | >0.98 | 0.980 | 0.954 | >0.98 | >0.98 | >0.98 | 0.89 | 0.85 | 0.78 |
| | PDA(g) | 0.39 | 3.0 | 3.9 | 3.9 | 3.9 | 3.0 | 3.5 | >0.95 | - | - | - | - | - | - | - | - |
| | MY Malt(g) | - | - | - | - | - | - | - | - | - | - | - | - | - | 2 | 2 | 2 |
| | Yeast(g) | - | - | - | - | - | - | - | - | 0.5 | 0.5 | 0.5 | 0.5 | 0.5 | 0.3 | 0.5 | 0.5 |
| | Glucose concentration(%) | 0.2% | 2% | 10% | 20% | 40% | 8% | 2% | 2% | - | 40% | - | - | - | - | - | - |
| | Sucrose concentration(%) | - | - | - | - | - | 10% | 10% | 40% | 40% | - | 10% | 10% | 2% | 40% | 40% | 40% |
| | Agar(g) | 2 | - | - | - | - | - | - | - | 2 | 2 | 2 | 2 | 2 | 2.8 | 2.5 | 2.8 |
| | Glycerin(g) | - | - | - | - | - | - | - | - | - | - | - | - | - | 10 | 30 | 55 |
| Evaluation of cultivation | Anker | ○ | ○ | ○ | ○ | ○ | ○ | ○ | ○ | ○ | ○ | ○ | ○ | ○ | × | × | × |
| | Fusarium herbarum | × | × | ○ | ○ | ○ | ○ | ○ | ○ | ○ | ○ | ○ | ○ | × | × | × | × |
| | Fusarium sp. | ○ | ○ | ○ | ○ | ○ | ○ | ○ | ○ | ○ | ○ | ○ | ○ | ○ | × | × | × |

FIG. 20

| Kind of fungi to be tested | | Reference Example 1 | Reference Example 2 | Example 7 | Reference Example 4 | Reference Example 5 | Reference Example 6 |
|---|---|---|---|---|---|---|---|
| | | \multicolumn{7}{c}{Diameter of colony in each culture medium (mm)} |
| | Culture medium | PDA | PDA | MY | MY | MY | MY |
| 1. | *A. penicillioides* | 0 | 0 | 10 | 21 | 9 | 2 |
| 2. | *A. restrictus* | 0 | 0 | 8 | 16 | 9 | 0 |
| 3. | *Eurotium herbariorum* | 0 | 0 | 72 | 79 | 32 | 2 |
| 4. | *Wallemia sebi* | 2 | 3 | 6 | 7 | 7 | 2 |
| 5. | *A. flavus* | 52 | 62 | 69 | 26 | 3 | 0 |
| 6. | *A. fumigatus* | 64 | 75 | 57 | 3 | 0 | 0 |
| 7. | *A. niger* | 44 | 60 | >85 | 19 | 2 | 0 |
| 8. | *A. versicolor* | 8 | 13 | 25 | 9 | 3 | 0 |
| 9. | *Penicillium glabrum* | 18 | 34 | 40 | 11 | 2 | 0 |
| 10. | *P. rugulosum* | 10 | 18 | 22 | 8 | 0 | 0 |
| 11. | *C. sphaerospermum* | 9 | 9 | 26 | 12 | 3 | 0 |
| 12. | *C. cladosporioides* | 25 | 25 | 34 | 4 | 3 | 0 |
| 13. | *Fusarium* sp. | 45 | 54 | 57 | 7 | 0 | 0 |
| 14. | *Stachybotrys* sp. | 19 | 16 | 10 | 0 | 0 | 0 |

FIG. 21

| Kind of fungi to be tested | | Diameter of colony in each culture medium (mm) | | | | | | | |
|---|---|---|---|---|---|---|---|---|---|
| | Temperature | Example11 23°C | Example12 25°C | Example13 27°C | Reference Example7 30°C | Reference Example8 33°C | Reference Example9 35°C |
| 1. | A. penicillioides | 13 | 10 | 13 | 10 | 0 | 0 |
| 2. | A. restrictus | 12 | 5 | 6 | 0 | 0 | 0 |
| 3. | Eurotium herbariorum | 60 | 60 | 69 | 59 | 50 | 5 |
| 4. | Wallemia sebi | 6 | 6 | 6 | 6 | 0 | 0 |
| 5. | A. flavus | 70 | 67 | >85 | >85 | >85 | >85 |
| 6. | A. fumigatus | 48 | 40 | 53 | 66 | >85 | >85 |
| 7. | A. niger | >85 | 74 | >85 | 68 | 58 | 80 |
| 8. | A. versicolor | 27 | 25 | 30 | 26 | 10 | 0 |
| 9. | Penicillium glabrum | 39 | 38 | 47 | 46 | 17 | 0 |
| 10. | P. rugulosum | 26 | 26 | 35 | 31 | 25 | 0 |
| 11. | C. sphaerospermum | 30 | 30 | 26 | 11 | 4 | 0 |
| 12. | C. cladosporioides | 33 | 33 | 31 | 26 | 5 | 0 |
| 13. | Fusarium sp. | 52 | 50 | 60 | 65 | 52 | 27 |
| 14. | Stachybotrys sp. | 10 | 10 | 10 | 10 | 9 | 8 |

FIG. 23

| Sample No. | DNA chip analysis(fluorescent intensity of probe) | | | Kind of fungi included in Sample confirmed according to the ITS region sequence analysis | | |
|---|---|---|---|---|---|---|
| | Aspergillus viricola | Aspergillus penicillioides | Eurotium sp. | | | |
| 1 | 0 | 0 | 34172 | Eurotium sp. | – | – |
| 2 | 11 | 50 | 13 | Penicillium sp. | – | – |
| 3 | 5 | 34134 | 45828 | A. penicillioides | Eurotium sp. | Cladosporium sp. |
| 4 | 0 | 34298 | 32227 | A. penicillioides | Eurotium sp. | C.cladosporioides |
| 5 | 2 | 22100 | 10 | A. penicillioides | A. versicolor | C.cladosporioides |
| 6 | 22 | 67 | 17 | A. aculeatus | Penicillium sp. | Pestalotiopsis sp. |
| 7 | 4 | 0 | 0 | Phidiella diplodiella | Penicillium sp. | Pestalotiopsis sp. C.cladosporioides |
| 8 | 0 | 10 | 0 | C.cladosporioides | Pestalotiopsis sp. | – |
| 9 | 0 | 0 | 3 | C.cladosporioides | Penicillium sp. | – |
| 10 | 0 | 0 | 14 | A. aculeatus | C.cladosporioides | Diaporthe phaseolorum |
| 11 | 0 | 0 | 0 | A. aculeatus | C.cladosporioides | Penicillium sp. |
| 12 | 0 | 36 | 60 | C.cladosporioides | Penicillium sp. | – |
| 13 | 8 | 13 | 38 | C.cladosporioides | Penicillium sp. | Pestalotiopsis sp. |
| 14 | 0 | 0 | 7 | C.cladosporioides | Pestalotiopsis sp. | – |
| 15 | 0 | 2 | 6 | C.cladosporioides | A.flavus | Colletotrichum gloeosporioides |
| 16 | 0 | 0 | 0 | C.cladosporioides | Alternaria sp. | – |
| 17 | 0 | 11 | 0 | C.cladosporioides | C.sphaerospermum | Alternaria sp. Pestalotiopsis sp. |
| 18 | 0 | 13 | 10 | C. cladosporioides | Penicillium sp. | Leptosphaerulina sp. |
| 19 | 248 | 0 | 0 | C.cladosporioides | Penicillium sp. | – |
| 20 | 0 | 0 | 0 | C.cladosporioides | Nodulisporium sp. | – |

FIG. 24

| Sample No. | DNA chip analysis(fluorescent intensity of probe) | | | Kind of fungi included in Sample confirmed according to the ITS region sequence analysis (MAX 4 types of fungi/sample) | | | |
|---|---|---|---|---|---|---|---|
| | *Aspergillus viridis* | *Aspergillus penicillioides* | *Eurotium sp.* | | | | |
| 21 | 14 | 0 | 1 | *C. cladosporioides* | *Fusarium sp.* | — | — |
| 22 | 15 | 0 | 0 | *C. cladosporioides* | *Penicillium sp.* | *Phomopsis sp.* | — |
| 23 | 0 | 0 | 6 | *C. cladosporioides* | *Penicillium sp.* | *Dothideomycete sp.* | — |
| 24 | 0 | 8351 | 0 | *A. penicillioides* | — | — | — |
| 25 | 0 | 25 | 15 | *A. versicolor* | — | — | — |
| 26 | 12 | 0 | 1 | *C. cladosporioides* | *Pestalotiopsis sp.* | *Toxicocladosporium sp.* | — |
| 27 | 18 | 0 | 0 | *C. cladosporioides* | *Penicillium sp.* | — | — |
| 28 | 28 | 12 | 29 | *C. cladosporioides* | *Aureobasidium pullulans* | — | — |
| 29 | 0 | 49 | 0 | *Arthopyreniaceae sp.* | — | — | — |
| 30 | 21 | 3993 | 1 | *A. penicillioides* | *C. cladosporioides* | *Acremonium sp.* | *Ascomycete sp.* |
| 31 | 0 | 0 | 0 | *A. versicolor* | *A. sclerotiorum* | *C. cladosporioides* | *Leptosphaerulina chartarum* |
| 32 | 3 | 48646 | 52 | *A. penicillioides* | *C. cladosporioides* | — | — |
| 33 | 43 | 26051 | 8 | *A. penicillioides* | *C. cladosporioides* | — | — |
| 34 | 0 | 0 | 0 | *C. cladosporioides* | — | — | — |
| 35 | 118 | 52312 | 58160 | *A. penicillioides* | *Eurotium sp.* | *Leptosphaerulina chartarum* | *A. restrictus* |
| 36 | 3 | 11 | 0 | *Nigrospora oryzae* | — | — | — |
| 37 | 0 | 10 | 0 | *C. cladosporioides* | — | — | — |
| 38 | 3 | 11 | 93 | *C. cladosporioides* | *Toxicocladosporium sp.* | — | — |
| 39 | 0 | 1 | 0 | *C. cladosporioides* | *Penicillium sp.* | *Arthrostoma sp.* | — |
| 40 | 17 | 0 | 9 | *Dothideomycete sp.* | *Epicoccum nigrum* | — | — |

FIG. 25

| Sample No. | DNA chip analysis(fluorescent intensity of probe) | | | Kind of fungi included in Sample confirmed according to the ITS region sequence analysis (MAX 4 types of fungi/sample) | | | |
|---|---|---|---|---|---|---|---|
| | *Aspergillus vitricola* | *Aspergillus penicillioides* | *Eurotium sp.* | | | | |
| 41 | 5 | 0 | 0 | C. cladosporioides | — | — | — |
| 42 | 6081 | 47991 | 29 | A. vitricola | A. penicillioides | A. restrictus | Alternaria alternata |
| 43 | 13817 | 6317 | 10 | A. vitricola | A. penicillioides | A. restrictus | A. gracilis |
| 44 | 60 | 10467 | 25 | A. penicillioides | C. sphaerospermum | Pestalotiopsis sp. | — |
| 45 | 0 | 0 | 13 | C. cladosporioides | Sterigmatomyces sp. | Alternaria alternata | Eupenicillium sp. |
| 46 | 0 | 0 | 82 | Arthrinium sp. | — | — | — |
| 47 | 0 | 32829 | 12 | A. penicillioides | Penicillium sp. | Montagnulaceae sp. | — |
| 48 | 0 | 0 | 18 | A. versicolor | C. cladosporioides | — | — |
| 49 | 27 | 14670 | 12 | A. penicillioides | Cladosporium sp. | — | — |
| 50 | 8 | 38193 | 1 | A. penicillioides | — | — | — |
| 51 | 0 | 4 | 20 | Nylariales sp. | — | — | — |
| 52 | 0 | 9 | 55 | Leptosphaerulina sp. | — | — | — |
| 53 | 0 | 0 | 0 | Chaetomium globosum | — | — | — |
| 54 | 0 | 42096 | 6 | A. penicillioides | Ascomycota sp. | Phaeosporales sp. | — |
| 55 | 13 | 36710 | 0 | A. penicillioides | Flammulina | — | — |
| 56 | 0 | 0 | 25 | Phomopsis sp. | — | — | — |
| 57 | 0 | 0 | 34 | Aureobasidium pullulans | — | — | — |
| 58 | 0 | 60483 | 7 | A. penicillioides | — | — | — |
| 59 | 0 | 0 | 0 | Curvularia sp. | Botryosphaeria protearum | Arthrobotrys | Cochliobolus lunatus |
| 60 | 4 | 24122 | 0 | A. penicillioides | Rhodotorula mucilaginosa | — | — |

METHOD FOR DETECTING FUNGI, REACTION SOLUTION FOR PCR, AND CARRIER FOR DETECTING FUNGI

TECHNICAL FIELD

The present invention relates generally to a method for detecting fungi, e.g., a method for detecting a wide variety of fungi with a high degree of accuracy, a reaction solution for PCR, and a carrier for detecting fungi.

BACKGROUND ART

In recent years, in food manufacturing sites, clinical sites, environments for protecting cultural assets, it has become important to check the presence of microorganisms such as fungi to confirm safety, as well as to prevent the proliferation thereof.

In such inspection of fungi, in general, a morphology observation method (cultivation method) is generally conducted in which a sample is collected from the environment and then pre-cultivated, and then, after incubation of about 20 days in a culture medium which is optimum for the type of fungi, morphological features are observed, whereby fungi are identified (see Patent Document 1).

However, in this method, since cultivation is required to be conducted separately according to the type of fungi, the inspection process becomes complicated. In addition, since cultivation takes a long period of time, the cultivation method is not appropriate for inspection which requires promptness, such as detection indoors where people stay and inspection of foods, for example. Further, identification cannot be made unless fungi spore that shows morphological features of fungi is formed, resulting in wasting of time and labor.

Recently, in inspection of fungi, detection by a gene has been conducted. Specifically, after cultivating a sample collected from an environment, DNA is extracted from a cultivated cell, a target region is amplified by a PCR (polymerase chain reaction) method, and an amplified product is analyzed, thereby to identify fungi present in the sample. As a method for analyzing an amplified product, for example, a method in which the size of an amplified product is analyzed by electrophoresis or fungi present in a sample is identified by means of a DNA chip, to which a probe which connects complimentarily to an amplified product is fixed, or the like have been proposed (see Patent Documents 2 to 6).
Patent Document 1: JP-A-2007-195454
Patent Document 2: JP-A-2008-35773
Patent Document 3: JP-A-2008-278848
Patent Document 4: JP-A-2008-278861
Patent Document 5: JP-A-2010-4879
Patent Document 6: JP-A-2009-284832

However, even by such an identification method using genes, when the type of fungi are very similar, it is significantly difficult to identify the type of fungi only by the presence or absence of a single target gene or the size thereof. For example, this method is not suited to an inspection where the identification accuracy on the level of type is required.

In Patent Documents 2 to 4, identification is conducted by using the ITS region (Internal Transcribed Spacer) in the gene of various fungi as a region to be amplified. By identification of fungi based on the ITS region, a false positive reaction tends to occur more frequently as the number of type of fungi is increased, thereby lowering the accuracy of the inspection.

On the other hand, Patent Documents 5 and 6 each disclose identification by using the β-tubulin gene as a region to be amplified. In these documents, it is stated that a specific type of fungi can be detected by using the β-tubulin gene as a region for amplification.

However, if the β-tubulin gene alone is used as a region for amplification, as in the case where only the ITS region is used as a region for amplification, a false positive reaction may occur.

SUMMARY OF THE INVENTION

As a result of extensive studies, the inventors have found that, by using both the ITS region and the β-tubulin gene as the regions for amplification, a wide variety of types of fungi can be detected with a high degree of accuracy. In one aspect, one or more embodiments of the present invention have been made based on this finding. The inventors have also found conditions under which the ITS region and the β-tubulin gene can be amplified efficiently in the simultaneous reaction system.

In the meantime, as mentioned above, in the method for identifying fungi by the morphology, in order to allow morphological features to be exhibited, an optimum culture medium according to the type of fungi and a long-term cultivation may be required. Further, since a high level of skill is required for identification, it may not be suited to prompt inspection and simplification of an inspection.

Further, in the method by PCR and the sequence analysis, since cultivation may be conducted separately according to the type of fungi, a relatively long inspection period of about 14 days is required. Further, an analysis may be required to be conducted separately according to the type of fungi, and hence, it is not suited to the case in which multi-sample processing is required.

On the other hand, by a new detection method by using a DNA chip, theoretically, a plurality of types of fungi can be detected all at once. Therefore, this detection method is expected as a prompt and easy detection method.

Based on the humidity suited to the growth thereof, fungi are divided into xerophilic fungi (which prefer the dried state), xerophilous fungi (which can withstand the dried state) and hygrophilous fungi (which prefer the wet state), and they are required to be cultivated by different culture mediums suited to each. In the above-mentioned first and second methods which have been conventionally conducted in general, it was required to cultivate according to the type of fungi. Therefore, there was no concept that a plurality of fungi are mixed and cultivated, and then each of fungi is detected separately. Accordingly, the technology in which xerophilic fungi, xerophilous fungi and hygrophilous fungi are cultivated simultaneously and each of fungi is allowed to be detectable specifically was not realized in the past.

One or more embodiments of the present invention have been made in view of the above-mentioned circumstances, and is aimed at providing a method for detecting fungi, a reaction solution for PCR used therefor, and a carrier for detecting fungi by amplifying the ITS region and the β-tubulin gene in the genomic DNA of fungi in the sample and confirming the presence or absence of an amplified product thereof.

Further, One or more embodiments of the present invention are aimed at providing a method for detecting fungi in which a plurality of fungi are simultaneously cultivated in the same culture medium without being cultivated separately, and at the same time, they are mixed to extract genomic DNA all at once, and each of fungi is allowed to be specifically detectable.

In general, a method for detecting fungi according to one or more embodiments of the present invention may be a method for detecting fungi comprising the steps of amplifying DNA fragments including target regions of fungal DNA and confirming the presence or absence of an amplified product, wherein the ITS region and the β-tubulin gene are used as the target regions.

By using the ITS region and the β-tubulin gene in combination as the target regions for amplification, as compared with the case where only one of them is used as a target region, it is possible to reduce occurrence of a false positive reaction. Therefore, a wide variety of fungi can be detected with a higher degree of accuracy. Further, accurate and specific detection of various types of fungi over a wide range in an inspection for confirming the presence or absence of fungi may be enabled.

In the method for detecting fungi according to one or more embodiments of the present invention, when amplification of a target region is conducted by the PCR method, the concentration ratio of a primer set for amplifying the β-tubulin gene and a primer set for amplifying the ITS region may be 1:0.9 to 1:0.1.

If the concentration ratio of the primer sets are set as mentioned above, by conducting a PCR reaction by using a reaction solution for PCR containing these primer sets, both the ITS region and the β-tubulin gene can be efficiently amplified. Therefore, by detecting them simultaneously, inspection of fungi can be conducted in a further high degree of accuracy. The concentration ratio of a primer set for amplifying the β-tubulin gene and a primer set for amplifying the ITS region may be 1:0.5 to 1:0.25 since the amplification efficiency of both of them can be highest.

The reaction solution for PCR according to one or more embodiments of the present invention may be a reaction solution for PCR for amplifying a target region and comprises, as a primer set for amplifying the ITS region, a primer set provided with a forward primer composed of a base sequence represented by sequence No. 1 and a reverse primer composed of a base sequence represented by sequence No. 2, as a primer set for amplifying the β-tubulin gene, a primer set provided with a forward primer composed of a base sequence represented by sequence No. 3 and a reverse primer composed of a base sequence represented by sequence No. 4.

By configuring a reaction solution for PCR as mentioned above, both the ITS region and the β-tubulin gene in various types of fungi can be amplified. As a result, presence or absence of fungi can be judged based on amplified products of both of them, a wider range of fungi can be detected with a higher degree of accuracy.

The reaction solution for PCR according to one or more embodiments of the present invention may further comprise, as a forward primer for specifically amplifying *Cladosporium* sp., a primer composed of a base sequence represented by sequence No. 5.

By configuring a reaction solution for PCR as mentioned above, it is possible to amplify DNA fragments of *Cladosporium* sp. which cannot be amplified efficiently only by using a reaction solution for PCR containing primers each comprising a base sequence represented by sequence Nos. 1 to 4, whereby the *Cladosporium* sp. can be appropriately detected.

Further, the carrier for detecting fungi according to one or more embodiments of the invention may be one in which, according to one or two or more types of fungi, a probe having a base sequence selected from the ITS region and a base sequence selected from the β-tubulin gene are fixed.

By configuring the carrier for detecting fungi in this way, by dropwise addition of an amplified product obtained by amplifying the ITS region and the β-tubulin gene simultaneously to the carrier for detecting fungi, fungi having DNA which connects complementary to the base sequence of the probe can be detected. In this carrier for detecting fungi, according to the type of fungi, both a probe having a base sequence selected from the ITS region and a probe having a base sequence selected from the β-tubulin gene are fixed, it is possible to confirm whether fungi are present or not based on these probes. Then, by determining presence of fungi when detection is confirmed both in the ITS region and the β-tubulin gene, it is possible to suppress the case where fungi are confirmed to be present based on the false positive determination, it is possible to detect fungi with a higher degree of accuracy.

The method for detecting fungi according to one or more embodiments of the present invention may comprise the steps of cultivating a plurality of types of fungi, mixing the plurality of types of fungi thus cultivated, extracting genomic DNA all at once, and detecting each of the plurality of types of fungi simultaneously and specifically.

By the above-mentioned method for detecting fungi of one or more embodiments of the present invention, even if fungi are cultivated in a mixed state without being separated according to the type of fungi, it is possible to detect the cultivated types of fungi specifically. That is, even if extraction of genomic DNA of each of fungi all at once in a state where a plurality of types of fungi which have been cultivated are mixed, each of fungi can be detected by a DNA chip.

As the method for detecting extracted genomic DNA by means of a DNA chip, common methods can be used.

Specifically, for example, by using a reaction solution for PCR including a primer set for amplifying a specific region of fungi to be detected, a specific region of genomic DNA is amplified by a PCR method. A probe which has been selected in advance from the region for amplification by this primer set is immobilized to a DNA chip. At this time, the primer set and the probe are required to be prepared in advance according to the specific region of fungi to be detected. Then, an amplified product obtained by the PCR method is added dropwise to the DNA chip, and the amplified product connected to the probe is detected, whereby various fungi contained in the mixture can be independently detected specifically.

Further, in the method of inspecting fungi according to one or more embodiments of the present invention, at least two or more types of fungi selected from the group consisting of xerophilic fungi, xerophilous fungi and hygrophilous fungi may be simultaneously cultivated in a prescribed single culture medium and each of the cultivated fungi may be simultaneously and specifically.

According to the method for inspecting fungi of one or more embodiments of the present invention, it is possible to cultivate fungi which are normally cultivated separately due to their preference to different humidity environments in a single culture medium simultaneously. Further, it is possible to detect each of fungi specifically from the mixture of these. Therefore, without considering the nature or the like of fungi, it is possible to cultivate fungi simultaneously all at once, whereby simplification of inspection of fungi can be realized.

In the above-mentioned method for inspecting fungi according to one or more embodiments of the present invention, it a plurality of types of fungi may be cultivated with a water active value of less than 1.0 and 0.90 or more, and a sugar concentration of 5 to 50%, or 10 to 40%. As for the type of sugar, glucose and sucrose may be used.

By a solid medium having such a water activity value and a sugar concentration, it is possible to cultivate any of xerophilic fungi, xerophilous fungi and hygrophilous fungi. That is, all types of fungi can be cultivated simultaneously all at once for detection.

Furthermore, in the method for inspecting fungi of one or more embodiments of the present invention, a plurality of types of fungi may be cultivated at a temperature of 25° C.±2° C.

Within such a temperature range, it becomes possible to allow any of xerophilic fungi, xerophilous fungi and hygrophilous fungi to be proliferated sufficiently.

In the method for inspecting fungi according to one or more embodiments of the present invention, it is possible to place a plurality of types of fungi which have been cultivated in a container in which beads for pulverizing physically the cell wall of fungi are accommodated, followed by mixing, and to extract genomic DNA all at once.

By the method for inspecting fungi according to one or more embodiments of the present invention mentioned above, it is possible to extract genomic DNA from a plurality of types of fungi which have been simultaneously cultivated.

In the method for inspecting fungi according to one or more embodiments of the present invention, the plurality of types of fungi may be fungi spores and mycellium floating in the air or adhered.

Due to such method for inspecting fungi of one or more embodiments of the present invention, it is possible to collect fungi in the environment and cultivate them as well as to detect them easily and simultaneously.

According to one or more embodiments of the present invention, a wide variety of fungi can be detected with a higher degree of accuracy.

Further, according to one or more embodiments of the present invention, it becomes possible to cultivate a plurality of types of fungi in the same culture simultaneously, and it becomes possible to extract genomic DNA all at once by mixing them and detect each of fungi specifically by means of a DNA chip.

BRIEF DESCRIPTION OF THE DRAWINGS

FIG. 2 is a view showing primers to be used in the method for detecting fungi according to one or more embodiments of the present invention;

FIG. 3 is a view showing probes used in the method for detecting fungi according to one or more embodiments of the present invention;

FIG. 4 is a view showing the type of fungi respectively contained in samples A to H which have been collected from an environment equipment, according to one or more embodiments of the present invention;

FIG. 19 is a view showing the cultivation evaluation of a cultivation test by using various culture compositions, according to one or more embodiments of the present invention;

FIG. 20 is a view showing the diameter of a colony when xerophilic fungi, xerophilous fungi and hygrophilous fungi are cultivated in various culture mediums, according to one or more embodiments of the present invention;

FIG. 21 is a view showing the diameter of a colony when xerophilic fungi, xerophilous fungi and hygrophilous fungi are cultivated at various temperatures, according to one or more embodiments of the present invention;

FIG. 23 is a view showing the results of a DNA chip analysis and a sequence analysis of the type of fungi of samples 1 to 20, according to one or more embodiments of the present invention;

FIG. 24 is a view showing the results of a DNA chip analysis and a sequence analysis of the type of fungi of samples 21 to 40, according to one or more embodiments of the present invention; and FIG. 25 is a view showing the results of a DNA chip analysis and a sequence analysis of the type of fungi of samples 45 to 60, according to one or more embodiments of the present invention.

DETAILED DESCRIPTION OF EMBODIMENTS OF THE INVENTION

Figure 1:
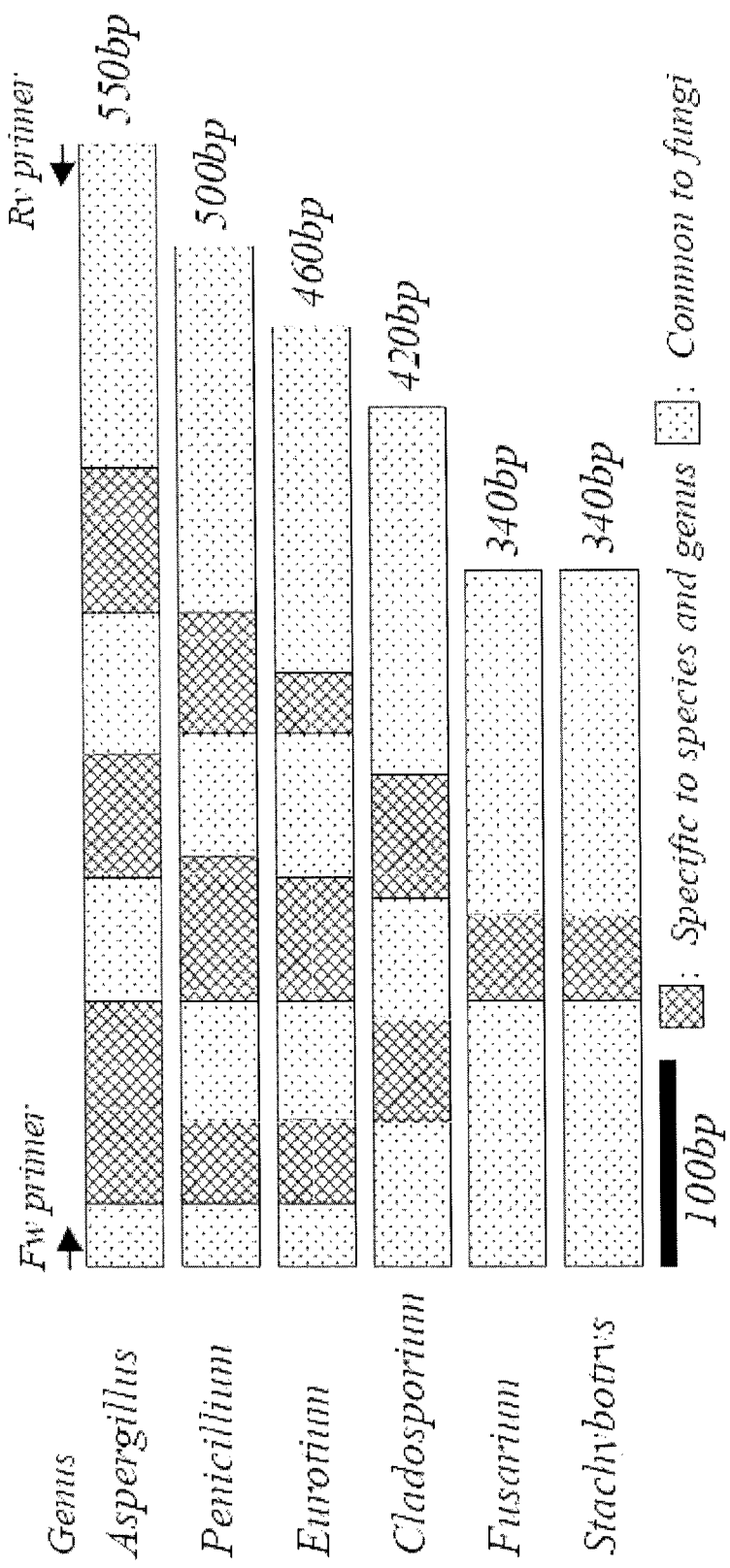
FIG. 1 is a view showing regions specific to the species or the genus and regions common to the fungi in the β-tubulin gene which have been PCR-amplified by a primer set formed of sequence No. 3 and sequence No. 4.

Hereinafter, a detailed explanation will be made on one embodiment of the method for detecting fungi, a reaction solution for PCR and a carrier for detecting fungi according to the present invention. However, the present invention is not limited to the following embodiment and the Examples given later.

[Method for Detecting Fungi]

The method for detecting fungi according to this embodiment is a method which comprises the steps of amplifying DNA fragments including a target region in fungal DNA and confirming the presence or absence of an amplified product, wherein the ITS region and the β-tubulin gene are used as a target region.

Although no specific restrictions are imposed on the type of fungi, but *Eurotium* sp., *Apergillus penicillioides*, *Aspergillus Section Restricti*, *Wallemia sebi*, *Aspergillus vitricola*, *Penicillium* sp., *Aspergillus Section Fumigati*, *Aspergillus Section Flavi*, *Aspergillus Section Nidulantes*, *Aspergillus Section Nigri*, *Stachybotrys chartarum*, *Fusarium solani*, *Cladosporium* sp. or the like can be used as fungi to be detected in the method for detecting fungi, a reaction solution for PCR and a carrier for detecting fungi. In addition, fungi such as *Fusarium oxysporum*, *Fusarium graminiarum*, *Fusarium veriticilloides*, *Pythium ultimum*, *Colletorichum gloeosporioides*, *Colletorichum acutatum*, *Verticillum dahiae*, *Verticillium albo-atrum*, *Alternaria alternate*, *Trichlophyton rubrum*, *Trichophyton tonsurans*, and *Trichoderma viride* or the like can be used as fungi to be detected.

The target region in the method for detecting fungi in this embodiment means a region to be amplified in the fungal DNA. A specific spacer, a gene or the like can be used as such a region. In the present invention, as such a target region, both of the ITS region (Internal Transcribed Spacer) region and the β-tubulin gene may be used simultaneously.

The method for amplifying a DNA fragment including a target region is not particularly restricted. A PCR (polymerase chain reaction) method can be used.

In the PCR method, by using a reaction solution for PCR containing a primer set for amplifying target regions, specific regions in a fungal DNA are amplified. As a PCR apparatus, a common thermal cycler or the like can be used, and the PCR can be conducted under the following reaction conditions:

(a) 95° C. 10 minutes, (b) 95° C. (DNA denaturing process) 30 seconds, (c) 56° C. (annealing process) 30 seconds, (d) 72° C. (DNA synthesis process) 60 seconds, ((b) to (d) are repeated 40 cycles), (e) 72° C., 10 minutes As the method for confirming the presence or absence of an amplified product, a method by electrophoresis or detection by using a DNA chip or the like can be used.

In the electrophoresis method, by using, for example, MultiNA® (manufactured by Shimadzu Corporation), microcapillary electrophoresis causes an amplified product of PCR to be subjected to electrophoresis, and based on the position, the size of the band is confirmed, whereby it is possible to determine whether a correct amplified product has been obtained or not.

In the method by a DNA chip, probes which hybridize specifically to target regions are fixed to a DNA chip in advance. By adding dropwise to this DNA chip an amplified product of PCR, a label of the amplified product is detected, it is possible to judge whether a correct amplified product has been obtained. Detection of the label can be carried out by using a common label detection device such as a fluorescent scanning device. For example, it can be measured by measuring the fluorescent intensity of an amplified product by using BIOSHOT of Toyo Kohan Co., Ltd.

Further, the label is not limited to fluorescence, and other labels may be used.

In this embodiment, as primers, a primer set for amplifying the ITS region in a fungal DNA and a primer set for amplifying the β-tubulin gene are used.

The ITS region is a region which is spliced after being transformed to RNA. Therefore, as compared with a coding region, the ITS region has a low storage stability and is full of variety. However, since the ITS region is very similar between the types of fungi, the possibility that a false positive reaction occurs is relatively high. Therefore, when probes of a large variety of fungi are fixed to a DNA chip in order to distinguish fungi, if only probes selected from the ITS region are used, lowering in detection accuracy may occur.

On the other hand, when verifying the similarity of the β-tubulin gene between a plurality of types of fungi, as shown in FIG. 1, unique sequences are present in a relatively large amount according to each type of fungi, these areas are thought to be optimum for highly specific probe design.

Therefore, when both the ITS region of the β-tubulin gene were used as the target regions and verification was conducted for a wide variety of fungi, by using these regions in combination, it was revealed that occurrence of a false positive reaction could be appropriately reduced.

In the method for detecting fungi according to this embodiment, by using both the ITS region and the β-tubulin gene as target regions, a wide variety of fungi can be detected with a high degree of accuracy.

[Reaction Solution for PCR]

In the method for detecting fungi as mentioned above, the reaction solution for PCR according to this embodiment is used when amplification of DNA fragments containing a target region is conducted by the PCR method. As the reaction solution for PCR, it is possible to use one having the following composition. Specifically, it is possible to use a solution for PCR containing a nucleic acid synthetic substrate (dNTPmixture (dCTP, dATP, dTTP, dGTP)), primer sets, a nucleic acid synthesis enzyme (such as Nova Taq polymerase), a labeled component (such as Cy5-dCTP), genomic DNA of the sample, a buffer solution, and water as a remaining capacity component. Note that, as a buffer solution, Ampdirect® (manufactured by Shimadzu. Corporation) can be used, for example.

As the primer set in the reaction solution for PCR according to this embodiment, a primer set composed of a forward primer and a reverse primer capable of amplifying an ITS region in fungal DNA and a primer set composed of a forward primer and a reverse primer capable of amplifying a β-tubulin gene in fungal DNA are used.

No specific restriction are imposed on the primer set used in the reaction solution for PCR in this embodiment as long as it contains a primer set for amplifying the ITS region and a primer set for amplifying the β-tubulin gene. Specifically, the following primer sets can be used, for example. That is, as shown in FIG. 2, as the primer set for amplifying the ITS region, a primer set having a forward primer composed of a base sequence shown in sequence No. 1 and a reverse primer composed of a base sequence shown in sequence No. 2 can be used. Further, as a primer set for amplifying the β-tubulin gene, a primer set composed of a forward primer composed of a base sequence shown in sequence No. 3 and a reverse primer composed of a base sequence shown in sequence No. 4 can be used.

It is also possible that the concentration ratio of the primer set for amplifying the β-tubulin gene and the primer set for amplifying the ITS region be 1:0.9 to 1:0.1. Due to such a concentration ratio of the primer sets, these regions to be amplified can be amplified.

Here, in fungal DNA, the ITS region is present in a quantity of 100 copies or more. On the other hand, only one copy is present for the β-tubulin gene. Further, the size of an amplified product of the ITS region by the PCR method is about 250 bp, the size of an amplified product of the β-tubulin gene by the PCR method is 350 to 550 bp.

Therefore, if the concentration of the primer set for amplifying the β-tubulin gene and the concentration of the primer sets for amplifying the ITS region are the same in the reaction solution for PCR, an amplified product of the β-tubulin gene cannot be obtained in a sufficient amount, thereby leading to lowering in accuracy of detection.

On the other hand, if the concentration of the primer set for amplifying the ITS region in the reaction solution for PCR is decreased excessively, the effects of amplifying the ITS region may become small.

Therefore, as the concentration ratio of the primer set for amplifying the β-tubulin gene and the primer set for amplifying the ITS region, an optimum conditions for the concentration ratio are required to be found.

As a result of extensive studies on various concentration ratios, the inventors of the present invention have found that, both the ITS region and the β-tubulin gene can be amplified by the above-mentioned concentration ratio. In particular, the concentration ratio of the primer set for amplifying the β-tubulin gene and the primer set for amplifying the ITS region is allowed to be 1:0.5 to 1:0.25. The reason is that, when fungi is detected based on the fluorescent intensity after conducting fluorescence labeling of an amplified product, the fluorescence of the ITS region and the β-tubulin gene can be obtained at a high intensity.

The reaction solution for PCR of this embodiment may contain a primer for specifically amplifying *Cladosporium* sp. As such a primer, it is possible to use a forward primer composed of a base sequence shown in sequence No. 5 of FIG. 2, for example.

Here, if the primer set for amplifying the ITS region and the primer set for amplifying the β-tubulin gene are used, although an amplified product can be obtained by PCR for the β-tubulin gene of *Cladosporium* sp., a probe selected from a sequence which is complementary to the β-tubulin gene and the amplified product cannot be hybridized sufficiently, whereby *Cladosporium* sp. could not be detected appropriately.

As for *Cladosporium* sp., a forward primer which can specifically detect this fungus was added to the reaction solution for PCR, and a new amplified product was obtained. As explained later in detail in Examples, this type of fungi could appropriately be detected when this new amplified product was added dropwise to a carrier for detecting fungi of this embodiment.

That is, this forward primer which is for appropriately amplifying *Cladosporium* sp. is used to amplify the β-tubulin gene. By constituting a pair with a reverse primer shown in sequence No. 4, this forward primer can amplify the β-tubulin gene of *Cladosporium* sp.

The final concentration of the forward primer specific to *Cladosporium* sp. in the reaction solution for PCR may be 0.5 µM or less, e.g., 0.125 µM to 0.5 µM. Within such a range of the final concentration of the forward primer specific to *Cladosporium* sp. it is possible to detect *Cladosporium* sp.

Further, by allowing the final concentration of the forward primer specific to *Cladosporium* sp. to be 0.25 µM to 0.5 µM, it is possible to detect *Cladosporium* sp. In particular, a final concentration of 0.25 µM may be advantageous in one or more embodiments, since it is possible to almost minimize the effects exerted on the detection of other types of fungi.

The sequence of each primer in the above-mentioned primer set is not limited to the above-mentioned base sequence, and it is possible to use a sequence which has been appropriately modified within the range that fulfils the same function. That is, it can be a base sequence in which one or few bases are missing, substituted or added. It is also possible to allow it to be hybridized under stringent conditions to the nucleic acid fragment comprising a nucleotide sequence complementary to the respective base sequence.

The stringent conditions refer to conditions under which a specific hybrid is formed and a non-specific hybrid is not formed. For example, they are the conditions under which DNA having a high degree of homology (homology of 90% or more, 95% or more) relative to the above-mentioned primer set hybridizes with a DNA consisting of a base sequence complementary to the primer set. Generally, at a temperature which is lower than the melting point (Tm) of a perfect hybrid by about 5° C. to about 30° C., or about 10° C. to about 25° C., hybridization occurs. For stringent conditions, conditions described in J. Sambrooks et al, "Molecular Cloning, A Laboratory Manual, Second Edition, Cold Spring Harbor Laboratory Press (1989)", in particular, section 11.45 "Conditions for Hybridizing of Oligonucleotide Probes" or the like can be used.

[Carrier for Detecting Fungi]

The carrier for detecting fungi according to this embodiment is characterized in that, according to one or two or more types of fungi, a probe having a base sequence selected from the ITS region and a probe having a base sequence selected from the β-tubulin gene are fixed, and can be configured by using a DNA chip or the like.

Thus, the carrier for detecting fungi of this embodiment is provided with both a probe connecting with an amplified product of the ITS region and connecting with an amplified product of the β-tubulin gene according to the type of fungi. By judging as a positive fungi in which fluorescence is detected in both probes, it is possible to approximately eliminate improper judgment based on the false positive reaction.

Specifically, as shown in FIG. 3, for example, the following probe can be used according to the type of fungi.

That is, as a probe for detecting *Eurotium* sp., at least any of a probe having a base sequence shown in sequence No. 6 or 7 selected from the ITS region and a probe having a base sequence shown in sequence No. 8 selected from the β-tubulin gene can be used.

Further, as a probe for detecting *Aspergillus penicillioides*, at least any of probes having a base sequence shown in sequence Nos. 9 to 11 selected from the ITS region and a probe having a base sequence shown in sequence No. 12 selected from the β-tubulin gene can be used.

As a probe for detecting *Aspergillus vitricola*, at least any of a probe having a base sequence shown in sequence No. 13 or 14 selected from the ITS region and a probe having a base sequence shown in sequence No. 15 selected from the β-tubulin gene can be used.

As a probe for detecting *Aspergillus Section Restricti*, at least any of probes having a base sequence shown in sequence Nos. 16 to 20 selected from the ITS region and a probe having a base sequence shown in sequence No. 21 selected from the β-tubulin gene can be used.

As a probe for detecting *Aspergillus Section Nidulantes*, a probe having a base sequence shown in sequence No. 22 selected from the ITS region and a probe having a base sequence shown in sequence No. 23 selected from the β-tubulin gene can be used.

As a probe for detecting *Aspergillus Section Fumigati*, a probe having a base sequence shown in sequence No. 24 selected from the ITS region and a probe having a base sequence shown in sequence No. 25 selected from the β-tubulin gene can be used.

As for a probe for detecting *Aspergillus Section Flavi*, a probe having a base sequence shown in sequence No. 26 selected from the ITS region and a probe having a base sequence shown in sequence No. 27 selected from the β-tubulin gene can be used.

As a probe for detecting *Penicillium* sp., at least any of a probe having a base sequence shown in sequence No. 28 or 29 selected from the ITS region and at least any of probes having a base sequence shown in sequence Nos. 30 to 32 selected from the β-tubulin gene can be used.

As a probe for detecting *Stachybotrys chartarum*, a probe having a base sequence shown in sequence No. 33 selected from the ITS region and a probe having a base sequence shown in sequence No. 34 selected from the β-tubulin gene can be used.

As a probe for detecting *Fusarium solani*, a probe having a base sequence shown in sequence No. 35 and a probe having a base sequence shown in sequence No. 36 selected from the β-tubulin gene can be used.

As a probe for detecting *Cladosporium* sp., a probe having a base sequence shown in sequence No. 37 and at least any of a probe having a base sequence shown in sequence No. 38 or 39 can be used.

As a probe common to fungi, a probe having a base sequence shown in sequence No. 40 selected from the ITS region and a probe having a base sequence shown in sequence No. 41 selected from the β-tubulin gene can be used.

The carrier for detecting fungi of this embodiment is one in which one or more of the above-mentioned probe groups for detecting each of fungi is fixed.

As mentioned above, in the carrier for detecting fungi of this embodiment, by fixing probes which respectively are connected to an amplified product of the ITS region and the β-tubulin gene, occurrence of incorrect judgment based on the false positive reaction is reduced, whereby a wide range of fungi can be detected with a high degree of accuracy.

The carrier for detecting fungi of this embodiment can be used by a common method. Although no specific restrictions are imposed on the method, the carrier can be used as follows, for example.

First, an amplified product of PCR obtained by the method for detecting fungi according to this embodiment is mixed with one obtained by adding 0.3% SDS (sodium dodecyl sulfate) to a buffer (3×SSC citric acid–physiological saline), and the resultant is added dropwise to the carrier for detecting fungi of this embodiment.

After allowing this carrier for detecting fungi to stand at 45° C. for 1 hour, a PCR product which was not hybridized is washed away from the carrier for detecting fungi by using the above-mentioned buffer. The carrier is then mounted in a label detecting apparatus to measure the fluorescence intensity, whereby detection of fungi can be conducted.

As for each of the above-mentioned probes to be fixed to the carrier for detecting fungi of this embodiment, as in the case of the sequence of each primer in the above-mentioned primer set, it is possible to use a probe which has been appropriately modified as long as it fulfils the same function. That is, it can be a base sequence in which one or several bases are missing, substituted or added. Further, it is possible to allow the probe to be one which can be hybridized under stringent conditions to the nucleic acid fragment comprising a base sequence complementary to each base sequence.

Further, as probes to be fixed to the carrier for detecting fungi of this embodiment, in addition to the above-mentioned probe, a probe having a base sequence complementary to one in which one or several bases are missing, substituted or added in the respective base sequence, or one having a base sequence complementary to a probe which can be hybridized under stringent conditions to the nucleic acid fragment comprising a base sequence can be used.

Here, an amplified product obtained by the PCR method in the method for detecting fungi of this embodiment includes a nucleic acid fragment having a base sequence complementary to a nucleic acid fragment which is hybridized with the above-mentioned probe. Therefore, a base sequence complementary to the sequence Nos. 6 to 41 shown in FIG. 3 and a probe comprising a base sequence which is equivalent to these sequences can be hybridized with a nucleic acid fragment having a base sequence which is complementary to nucleic acid fragments which are hybridized with the above-mentioned probe.

Accordingly, when a probe comprising a base sequence complementary to the sequence Nos. 6 to 41 shown in FIG. 3 and a probe comprising a base sequence which is equivalent to these, i.e. a probe in which one or several bases are missing, substituted or added in each base sequence of the sequence Nos. 6 to 14 or one which can be hybridized to a nucleic acid fragment comprising a base sequence complementary to each base sequence under stringent conditions is fixed to the carrier for detecting fungi of this embodiment, each object fungi can be detected.

Next, one embodiment of the method for detecting fungi according to the present invention will be explained in detail. The method for detecting fungi according to this embodiment may be a method in which a plurality of types of fungi are cultivated, the plurality of types of fungi thus cultivated are mixed, genomic DNA are extracted all at once, and each of the plurality of types of fungi are simultaneously and specifically detected, and the method for detecting fungi is not limited to the following embodiment and examples.

The method for detecting fungi of this embodiment comprises the following steps.

(1) Collection of Fungi

First, by using an air sampler, air in a food manufacturing site, a clinical site, environments for protecting cultural assets or the like is collected. Then, the collected air is sprayed to an exclusive culture medium in the form of a strip for an air sampler.

As the culture medium, it is possible to use M40Y medium, MY10G medium, MY30G medium or the like, which can cultivate any of xerophilic fungi, xerophilous fungi and hygrophilous fungi, as explained later in the Examples. Among them, M40Y medium may be advantageous in one or more embodiments since it is possible to cultivate any of the above-mentioned fungi differing in nature highly efficiently.

As for the cultivation conditions, the fungi may be allowed to stand in a dark place of 23° C. to 27° C. for about 2 to 7 days.

Meanwhile, M40Y medium, MY10G medium and MY30G medium are thought to be a medium for cultivating xerophilic fungi and not suited to cultivation of hygrophilous fungi.

Then, the colony of various types of fungi are collected all at one without separating individually. Then, for example, after placing the collected samples in a vial or the like which has been charged with φ0.5 mm zirconia beads, the sample was frozen by immersing the vial in liquid nitrogen. Thereafter, by using a shaker or the like, the cells of the fungi are crushed. No specific restrictions are imposed on the destruction method of the cells as long as DNA can be extracted. Cells may be crushed by other methods.

(2) Extraction of DNA

As the method for extracting genomic DNA from the sample in which the cells of fungi have been destroyed, a common method such as the CTAB method (Cetyl trimethyl ammonium bromide), a method using a DNA extraction apparatus or the like can be used.

(3) Amplification of ITS region by PCR Method

Subsequently, by adding a primer set capable of amplifying the ITS1 region of rDNA of each of fungi is added to a reaction solution for PCR, and the specific region in genomic DNA of fungi in the above-mentioned sample is amplified. Specifically, as the forward primer and the reverse primer, one having a base sequence shown in sequence No. 42 and one having a base sequence shown in sequence No. 43 can respectively be used. As the PCR apparatus, a common thermal cycler or the like can be used.

As the reaction solution for PCR in this embodiment, one having the following composition may be used. Specifically, nucleic acid synthesis substrate (dNTPmixture (dCTP, dATP, dTTP, dGTP), primer sets, a nucleic acid synthase (Nova Taq polymerase or the like), and a labeling component (Cy5-dCTP or the like), genomic DNA of the sample, a buffer, and water as the remaining capacitive component can be used. As a buffer, Ampdirect® (Shimadzu Corporation) can be used, for example.

As the PCR reaction conditions in the method for detecting fungi according to this embodiment, the following conditions may be used, for example.
(a) 95° C. 10 minutes, (b) 95° C. (DNA denaturing step) 30 seconds, (c) 56° C. (annealing process), 30 seconds, (d) 72° C. (DNA synthesis step), 60 seconds ((b) to (d) steps are repeated 40 cycles), (e) 72° C., 10 minutes (4) Detection by DNA Chip No specific restrictions are imposed on the DNA chip used in this embodiment as long as it is one in which a probe selected from DNA of fungi to be detected is fixed. For example, a spot type DNA chip and a composite type DNA chip can be used.

Specifically, a probe which is connected with an amplification region which is amplified by a primer set contained in a reaction solution for PCR is synthesized in advance, and immobilized on the substrate of the DNA chip. For example, as a probe for detecting *Aspergillus vitricola*, one composed of a base sequence represented by the sequence No. 44 can be used. Further, as a probe for detecting *Aspergillus penicillioides*, one composed of a base sequence represented by the sequence No. 45 can be used. As a probe for detecting *Eurotium* sp., one composed of a base sequence represented by the sequence No. 46 can be used.

Subsequently, a PCR amplified product is added dropwise to a DNA chip, a label of a PCR amplified product which has been hybridized on the above-mentioned probe for detecting fungi is detected. Specifically, it can be conducted by the following procedure.

First, a prescribed buffer is mixed with a PCR amplified product, and the resultant is added dropwise to a DNA chip.

Then, the DNA chip is allowed to stand at 45° C. for 1 hour. Thereafter, a PCR amplified product which has not been hybridized by the prescribed buffer is washed away from the DNA chip.

Then, the DNA chip is mounted in a label detection apparatus to detect the label, and judgment is conducted whether fungi to be detected are present or not. As the label detection apparatus, a common apparatus such as a fluorescent scanning apparatus can be used. The label or its detection method is not limited to fluorescence, and other methods may be used.

As explained above, according to the method for detecting fungi of this embodiment, a plurality of types of fungi can be simultaneously cultivated by using a culture medium capable of cultivating any of xerophilic, xerophious and hygrophilous fungi. Then, the cultivated fungi are mixed, and genomic DNA is extracted all at once, and by using a DNA chip, each of the plurality of types of fungi can be simultaneously and specifically detected.

Therefore, it is not necessary to cultivate the collected fungi separately, and a plurality of types of fungi can be detected all at one easily and promptly.

EXAMPLES

Hereinafter, the method for detecting fungi, a reaction solution for PCR and a test conducted by using a carrier for detecting fungi will be explained in detail.

(Test 1)

In the method for detecting fungi according to one or more embodiments of the present invention, in detecting various types of fungi by a DNA chip analysis using a multiplex PCR, in order to find a concentration range of each primer set in a PCR reaction solution which realizes simultaneous amplification of both the ITS region of the β-tubulin gene, Test 1 was conducted.

As the fungi to be detected, a wild fungi collected from the facility environment were used. That is, air in the facility environment was collected by using an air sampler, and the collected air was blown to each of the culture mediums A to D for cultivation. Cultivation was conducted by allowing the samples to stand in a dark place at 25° C. for 7 days.

Next, for each sample, part of colony of various types of fungi generated in the culture medium was collected separately, and cultivated separately in a dark place of 25° C. for 7 to 10 days. Each colony was subjected to a DNA sequence analysis to confirm the type of fungi thereof. The results are shown in FIG. 4. The DNA sequence analysis was entrusted to Takara Bio Inc. and conducted by means of a DNA sequencer. The same applies to the following.

Further, according to the sample, colony of various types of fungi generated in the culture medium were collected all at once and placed in a vial filled with φ0.5 mm zirconia beads. The vial was immersed in liquid nitrogen to allow the sample to be frozen. Then, by using a shaker, the cells of the fungi were crushed.

Then, according to the sample, genomic DNA of fungi was extracted by means of a DNA extracting apparatus. By the PCR method, the ITS region and the β-tubulin gene of each of fungi were simultaneously amplified.

At this time, as the primer set for amplifying the ITS region, a forward primer (F primer) comprising the base sequence represented by sequence No. 1 and a reverse primer (R primer) comprising the base sequence represented by sequence No. 2, both are shown in FIG. 2, are used. As the primer set for amplifying the β-tubulin gene, a forward primer comprising the base sequence represented by sequence No. 3 and a reverse primer comprising g the base sequence represented by sequence No. 4, both are shown in FIG. 2 are used. Both primer sets are synthesized by Operon Biotechnologies, Inc.

Further, as the reaction solution for PCR, for each of the samples A to D by means of Ampdirect® (manufactured by Shimadzu Corporation), a solution of the following composition was prepared in an amount of 20 μl.
1. Ampdirect (G/Crich) 4.0 μl
2. Ampdirect (addition-4) 4.0 μl
3. dNTPmix 1.0 μl
4. Cy-5dCTP 0.2 μl
5. ITS1-Fw primer (10 μM) 1.0 μl
6. ITS1-Rv primer (10 μM) 1.0 μl
7. BtF primer (10 μM) 1.0 μl
8. BtR primer (10 μM) 1.0 μl
9. Template DNA (for each sample A to D) 1.0 μl
10. NovaTaq polymerase 0.2 μl
11. Water (added until the total volume became 20.0 μl)

Further, four types of a reaction solution for PCR were prepared in the same manner as mentioned above, except that, as the primer for amplifying the ITS region, the forward primer and the reverse primer were compounded by the following amount ratios.
primer (9 μM) 0.9 μl
primer (8 μM) 0.8 μl
primer (5 μM) 0.5 μl
primer (2.5 μM) 0.25 μl
primer (1.25 μM) 0.125 μl
primer (1 μM) 0.1 μl
primer (0.625 μM) 0.0625 μl As for the final concentration ratio of the primer set for amplifying the β-tubulin gene and the primer set for amplifying the ITS region, according to samples A to D, the following five types of the concentration ratio were prepared, and a test was conducted for each ratio.

(i) 0.5 μM:0.5 μM
(ii) 0.5 μM:0.45 μM
(iii) 0.5 μM:0.40 μM
(iv) 0.5 μM:0.25 μM
(v) 0.5 μM:0.125 μM
(vi) 0.5 μM:0.0625 μM
(vii) 0.5 μM:0.050 μM
(viii) 0.5 μM:0.03125 μM By using each of the above-mentioned reaction solutions for PCR, by using a nucleic acid amplification apparatus (TaKaRa PCR Thermal Cycler Dice® Gradient, manufactured by Takara Bio Inc.), amplification of DNA was conducted under the following conditions.
(a) 95° C. for 10 minutes
(b) 95° C. for 30 seconds
(c) 56° C. for 30 seconds
(d) 72° C. for 60 seconds ((b) to (d) were repeated 40 cycles))
(e) 72° C. for 10 minutes As for the DNA chip, Gene Silicon® (manufactured by Toyo Kohan Co., Ltd.) was used. Of the probes shown in FIG. 3, one in which the following probes were immobilized was used.

<Probe Selected from the ITS Region>
(1) *Eurotium* sp. sequence Nos. 6 and 7
(2) *Aspergillus penicilloides* sequence Nos. 9 to 11
(3) *Aspergillus vitricola* sequence No. 13
(4) *Aspergillus Section Restricti* sequence Nos. 16 to 20
(5) *Aspergillus Section Nidulantes* sequence No. 22
(7) *Aspergillus Section Flavi* sequence No. 26
(8) *Penichillium* sp. sequence No. 28
(11) *Clandosporium* sp. sequence No. 37
(12) Common to fungi sequence No. 40

<Probe Selected from the β-tubulin Gene>
(1) *Eurotium* sp. sequence No. 8
(2) *Aspergillus penicilloides* sequence No. 12
(3) *Aspergillus vitricola* sequence No. 15
(4) *Aspergillus Section Restricti* sequence No. 21
(5) *Aspergillus Section Nidulantes* sequence No. 23
(7) *Aspergillus Section Flavi* sequence No. 27
(8) *Penichillium* sp. sequence No. 30
(12) Common to fungi sequence No. 41

Subsequently, a PCR amplified product was mixed with a buffer (3×SSC citric acid–physiological saline+0.3% SDS), and the resultant mixture was heated at 94° C. for 5 minutes, and added dropwise to the DNA chip.

This DNA chip was allowed to stand at 45° C. for 1 hour. By using the above-mentioned buffer, a PCR amplified product was washed away from the DNA chip.

Figure 5:
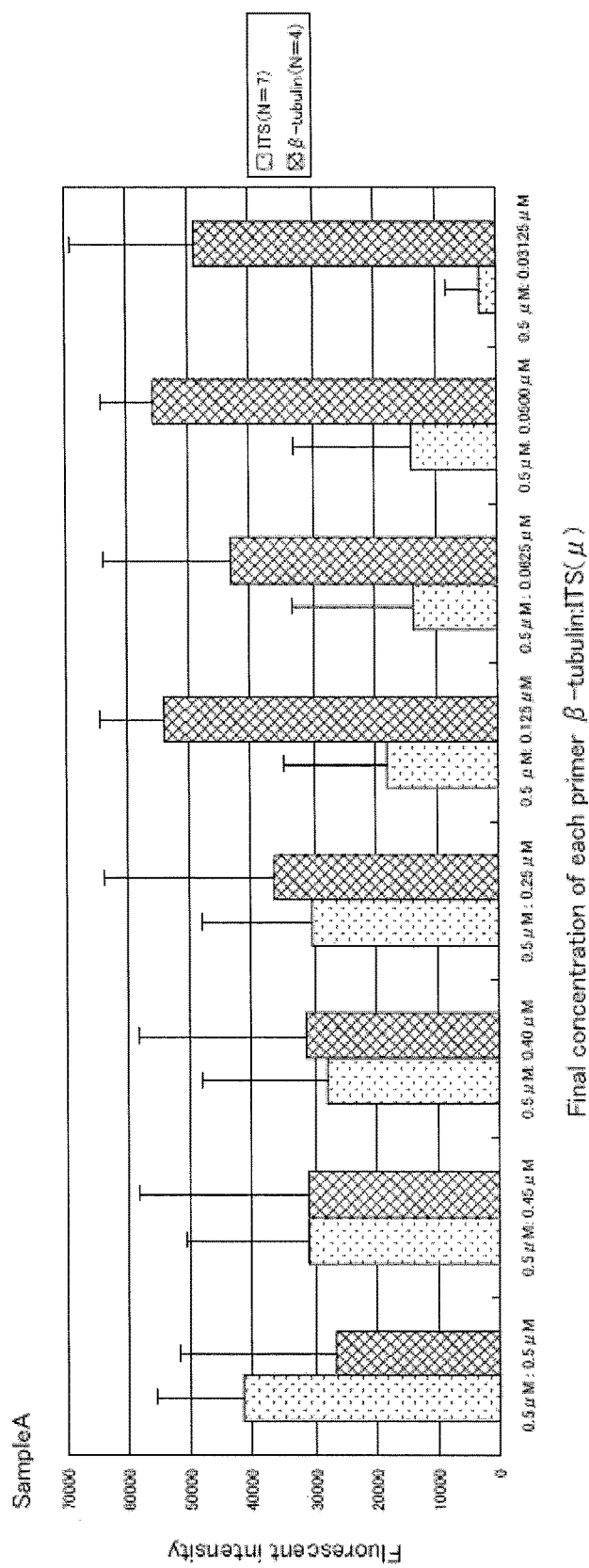
FIG. 5 is a view showing the results of test 1 (sample A) for finding the range of the primer set capable of detecting both the ITS region and the β-tubulin gene in the simultaneous reaction system, according to one or more embodiments of the present invention.
Figure 6:
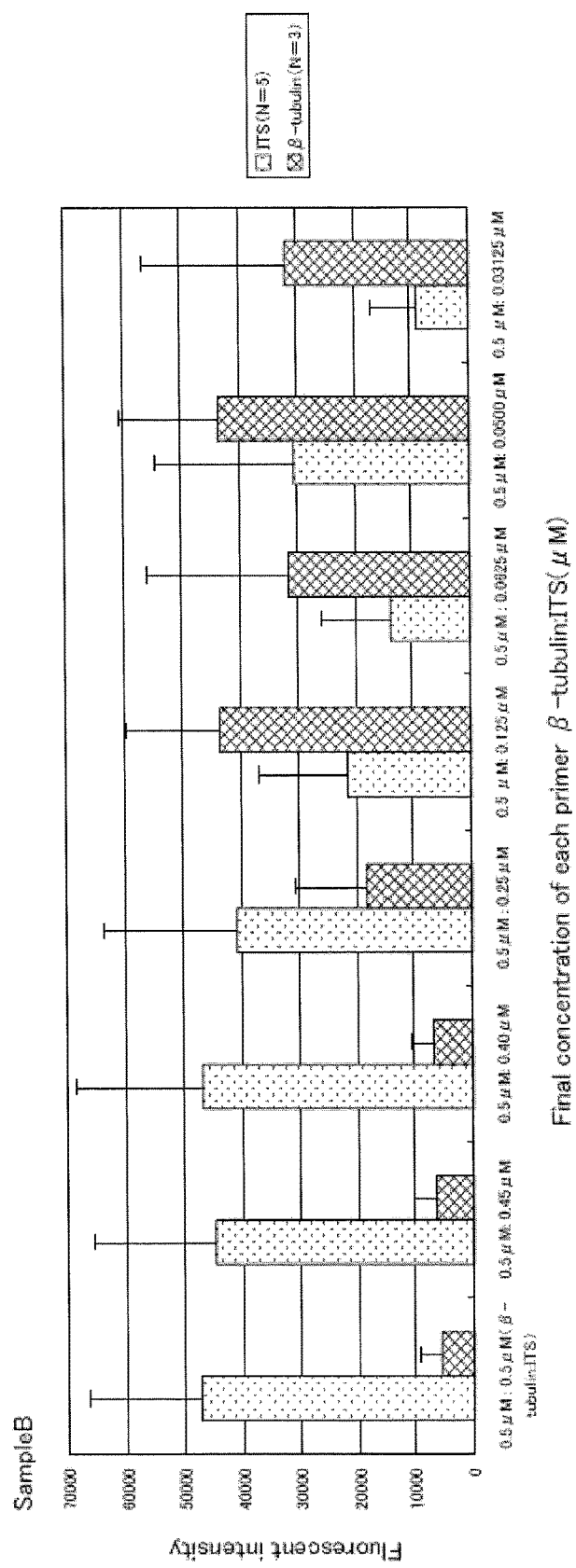
FIG. 6 is a view showing the results of test 1 (sample B) for finding the range of the primer set capable of detecting both the ITS region and the β-tubulin gene in the simultaneous reaction system, according to one or more embodiments of the present invention.
Figure 7:
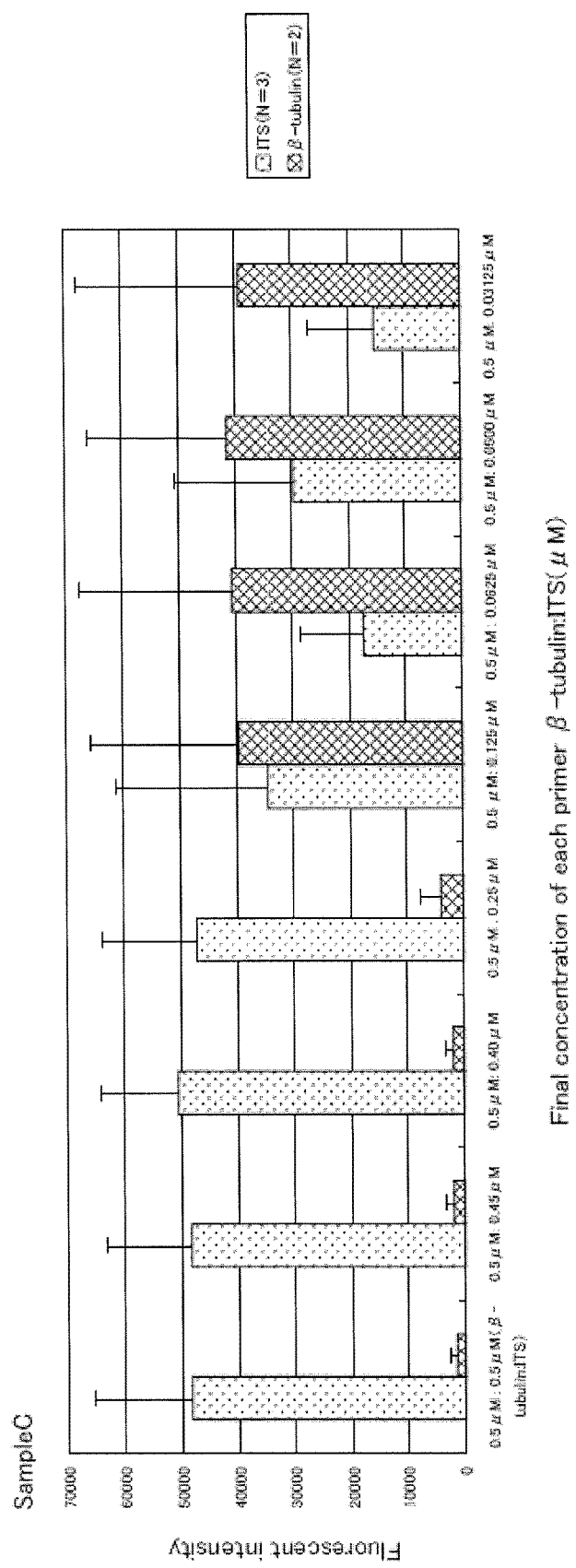
FIG. 7 is a view showing the results of test 1 (sample C) for finding the range of the primer set capable of detecting both the ITS region and the β-tubulin gene in the simultaneous reaction system, according to one or more embodiments of the present invention.
Figure 8:
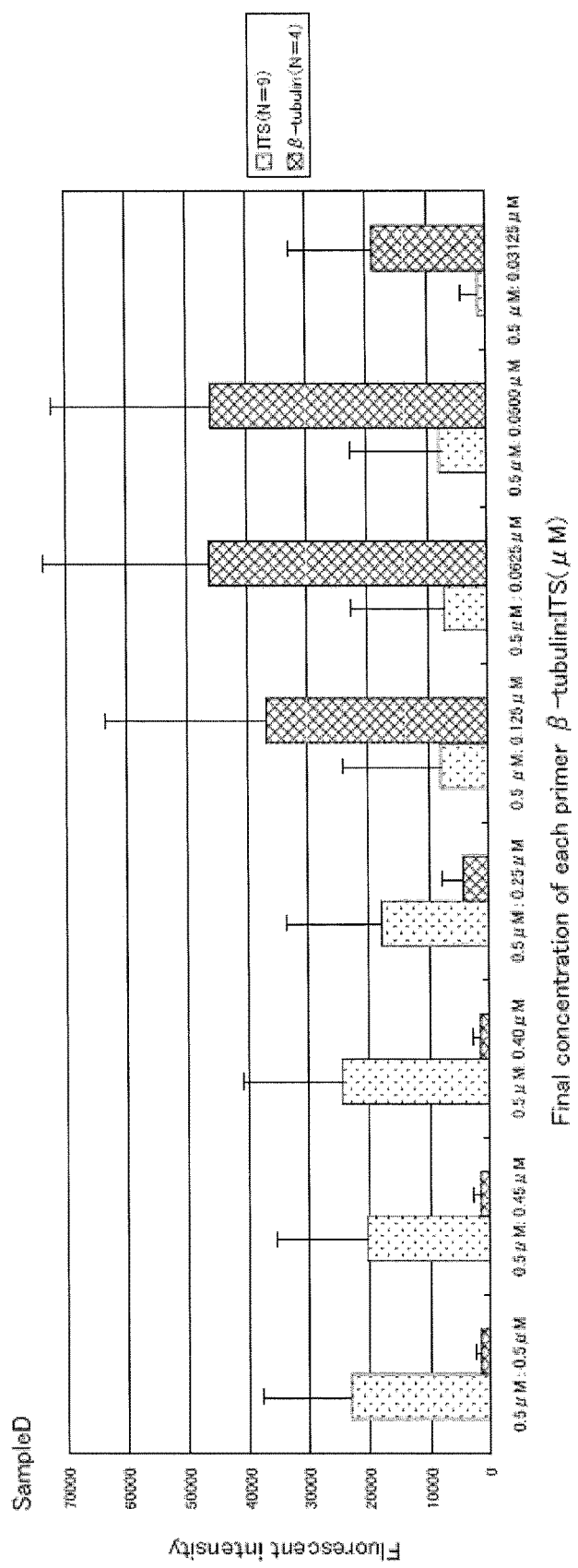
FIG. 8 is a view showing the results of test 1 (sample D) for finding the range of the primer set capable of detecting both the ITS region and the β-tubulin gene in the simultaneous reaction system, according to one or more embodiments of the present invention.

Subsequently, the DNA chip was mounted in a label detection apparatus (GenePix4100A, manufactured by Molecular Devices), and the fluorescent intensity in each probe was measured. According to the concentration ratio of the primer set, an average value of the fluorescent intensity in the probe for ITS region and the fluorescent intensity in the probe for the β-tubulin gene. The results obtained are shown in FIGS. 5 to 8. FIG. 5, FIG. 6, FIG. 7 and FIG. 8 respectively show the fluorescent intensity according to the various concentration ratios of the primer set, in which FIG. 5 shows the intensity using Sample A, FIG. 6 shows the intensity using Sample B, FIG. 7 shows the intensity using Sample C and FIG. 8 shows the intensity using Sample D.

Figure 9:
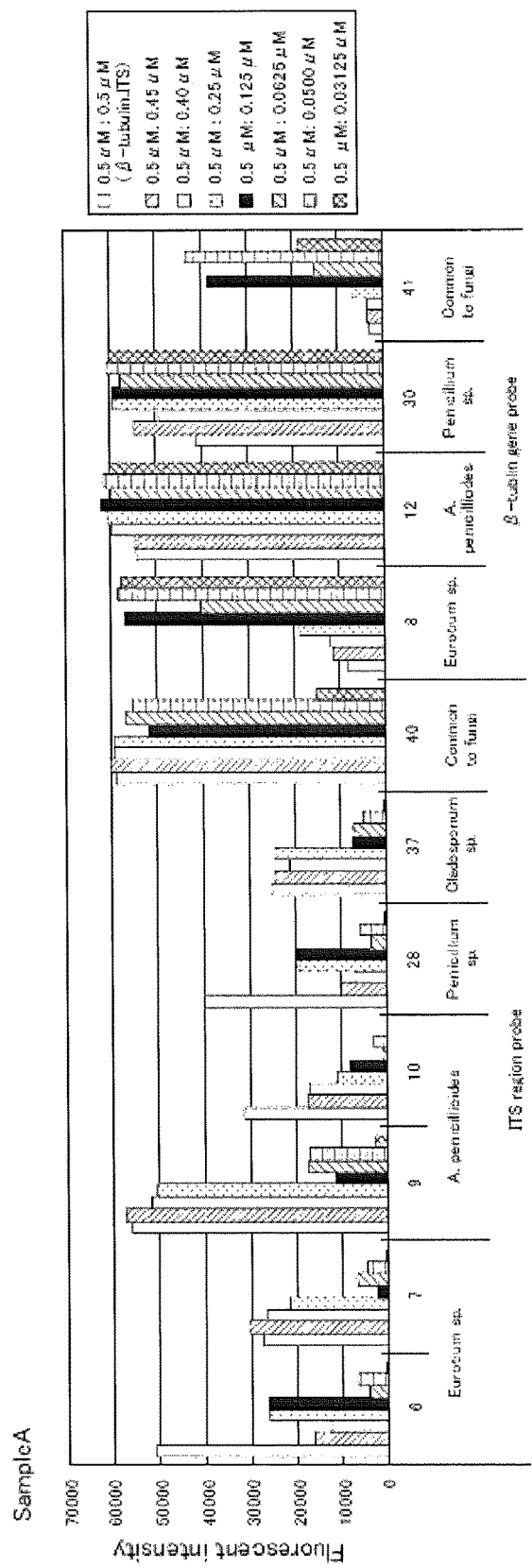
FIG. 9 is a view showing the fluorescent intensity according to the primer set concentration ratio and according to the probe for the sample A of test 1, according to one or more embodiments of the present invention.
Figure 10:
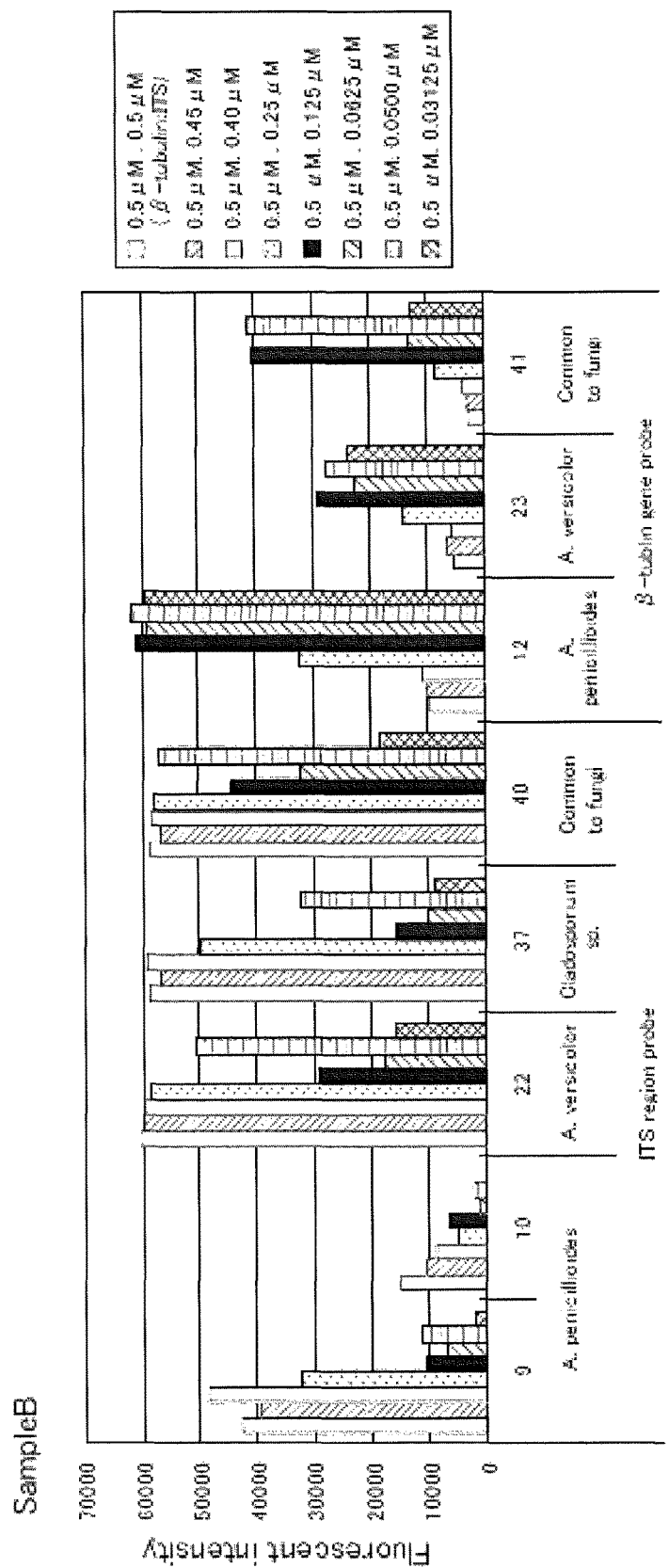
FIG. 10 is a view showing the fluorescent intensity according to the primer set concentration ratio and according to the probe for the sample B of test 1, according to one or more embodiments of the present invention.
Figure 11:
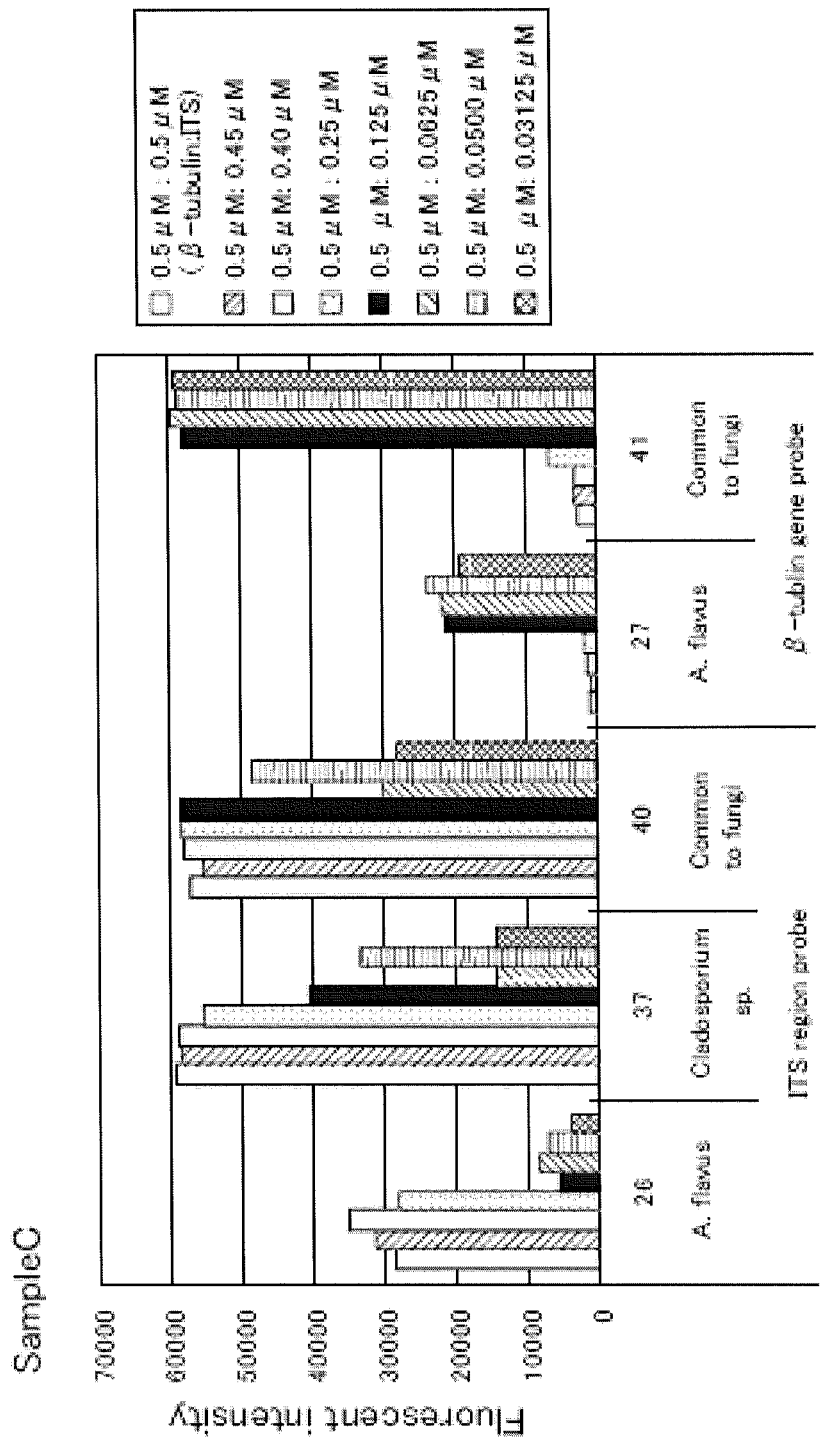
FIG. 11 is a view showing the fluorescent intensity according to the primer set concentration ratio and according to the probe for the sample C of test 1, according to one or more embodiments of the present invention.
Figure 12:
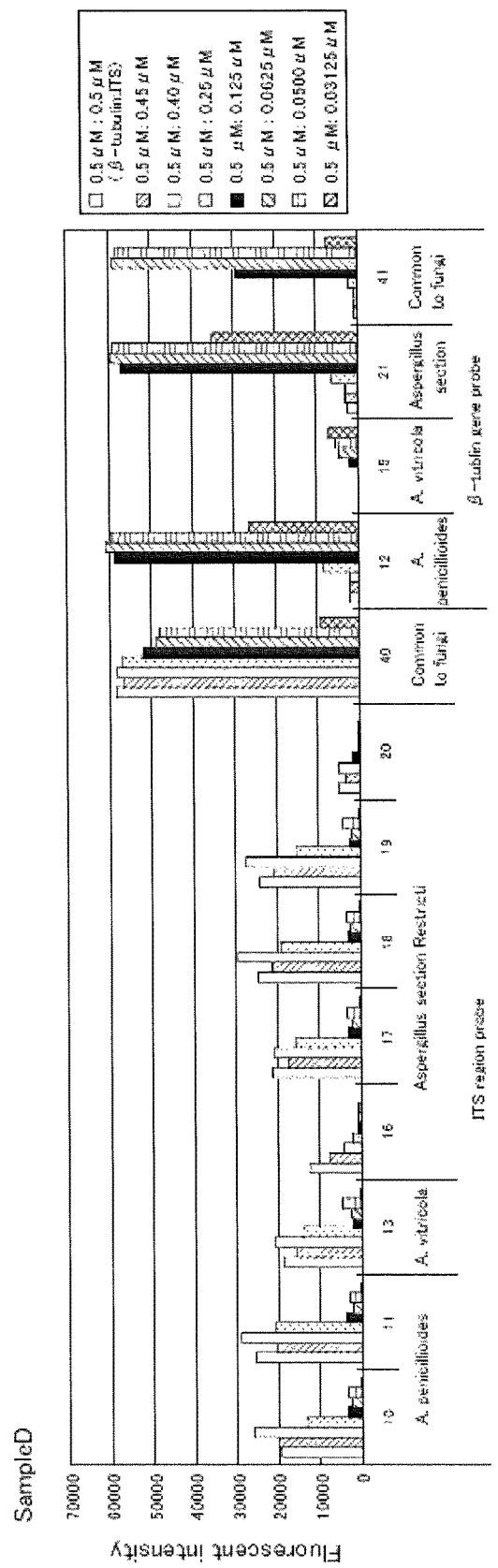
FIG. 12 is a view showing the fluorescent intensity according to the primer set concentration ratio and according to the probe for the sample D of test 1, according to one or more embodiments of the present invention.

FIGS. 9 to 12 show the fluorescent intensity according to the various concentration ratios of the primer set, in which FIG. 9 shows the intensity using Sample A, FIG. 10 shows the intensity using Sample B, FIG. 11 shows the intensity using Sample C and FIG. 12 shows the intensity using Sample D. The "N" in FIGS. 5 to 8 shows the number of probes in FIGS. 9 to 12. The same applies to FIG. 15.

(Test 2)

In order to confirm the relationship between the fluorescence intensity in the DNA chip analysis and the amount of an amplified product by PCR, test 2 was conducted.

Specifically, as for each of Samples B and C of test 1, PCR was conducted in the same manner as in test 1 by using five types of a reaction solution for PCR of which the ratio of the final concentration of the primer set for the β-tubulin gene and the final concentration of the primer set for the ITS region was as follows.

Figure 13:
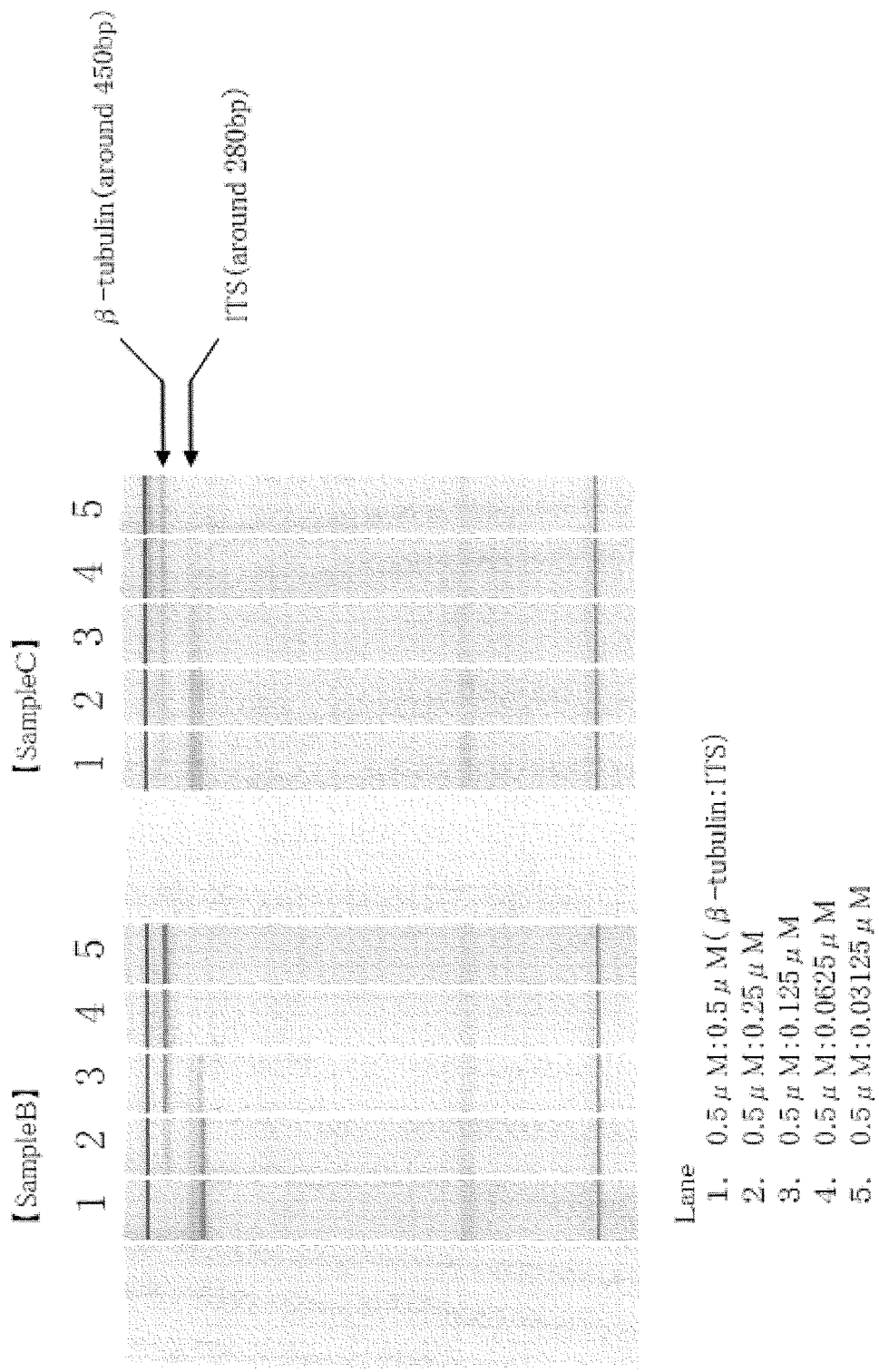
FIG. 13 is a view showing the results of test 2 for confirming the correlative relationship between the fluorescent intensity in the DNA chip analysis and the amount of an amplified product by PCR, according to one or more embodiments of the present invention.

(Lane 1) 0.5 μM:0.5 μM
(Lane 2) 0.5 μM:0.25 μM
(Lane 3) 0.5 μM:0.125 μM
(Lane 4) 0.5 μM:0.0625 μM
(Lane 5) 0.5 μM:0.03125 μM The resulting amplified product was analyzed by using MultiNA® (manufactured by Shimadzu Corporation). The results obtained are shown in FIG. 13.

As shown in the figure, in sample B, as for the β-tubulin gene, the band of lane 1 is indicated in a light color, the band of lane 2 is indicated in a slightly darker color, and the bands of lanes 3 to 5 are indicated in a dark color. As for the ITS region, the band of lanes 1 and 2 are dark, the band of the lane 3 is slightly dark and bands of lanes 4 and 5 are light. These results agree with the fluorescent intensity in the DNA chip analysis of Sample B shown in FIG. 6.

In sample C, as for the β-tubulin gene, the bands of lanes 1 and 2 are indicated in a light color and the bands of lanes 3 to 5 are indicated in a relatively dark color. For the ITS region, the bands of lanes 1 to 3 are indicated in a dark color and the bands of lanes 4 and 5 are indicated in a light color. These results agree with the fluorescent intensity in the DNA chip analysis of sample C shown in FIG. 7.

From the above, it was confirmed that the fluorescent intensity in the DNA chip analysis and the amount of an amplified product by PCR are related.

(Test 3)

In order to confirm the primer set capable of detecting both the ITS region and the β-tubulin gene simultaneously, the same test was conducted again by using a sample different from that used in test 1.

As the fungi to be detected, as in the case of test 1, those obtained by blowing wild fungi collected from the facility environment to each of culture mediums for Samples E to H, followed by cultivation, were used. The colonies of various fungi generated in the culture mediums for Samples E to H were incubated separately, and each colony was subjected to a DNA sequence analysis to confirm the type of fungi. The results are shown in FIG. 4.

For each sample, colonies of various fungi generated in the culture medium were collected all at once, and the cells of the fungi were crushed and genomic DNA was extracted. By the PCR method, the ITS region and the β-tubulin gene were amplified by the PCR method.

At this time, as the primer set, as in the case of test 1, a primer set for amplifying the ITS region comprising a base sequence shown in sequence No. 1 and a base sequence shown in sequence No. 2, a primer set for amplifying the β-tubulin gene comprising a base sequence represented by sequence No. 3 and a base sequence represented by sequence No. 4, both are shown in FIG. 2, were used.

As the reaction solution for PCR, for each of samples E to H, Ampdirect® (manufactured by Shimadzu Corporation) was used, 20 μl of a reaction solution having the following composition was prepared.

1. Ampdirect (G/Crich) 4.0 μl
2. Ampdirect (addition-4) 4.0 μl
3. dNTPmix 1.0 μl
4. Cy-5dCTP 0.2 μl
5. ITS1-Fw primer (5 μM) 0.5 μl
6. ITS1-Rv primer (5 μM) 0.5 μl
7. BtF primer (10 μM) 1.0 μl
8. BtR primer (10 μM) 1.0 μl
9. Template DNA (for each sample E to H) 1.0 μl
10. NovaTaq polymerase 0.2 μl
11. Water (added until the total quantity became 20.0 μl)

As the reaction solution for PCR, for each of samples E to H, was used, 20 μl of a reaction solution having the same composition as mentioned above, except that the composition of the primer for amplifying the ITS region was changed as follows:

ITS1-Fw primer (2.5 μM) 2.5 μM
ITS1-Rv primer (2.5 μM) 2.5 μM

As mentioned above, for each sample, two types of the reaction solution for PCR differing in final concentration of the primer set for amplifying the β-tubulin gene and the primer set for amplifying the ITS region; i.e. 0.5 μM:0.25 μM and 0.5 μM:0.125 μM, were prepared, and a test was conducted for each. The reaction conditions of PCR are the same as those for test 1.

Figure 14:
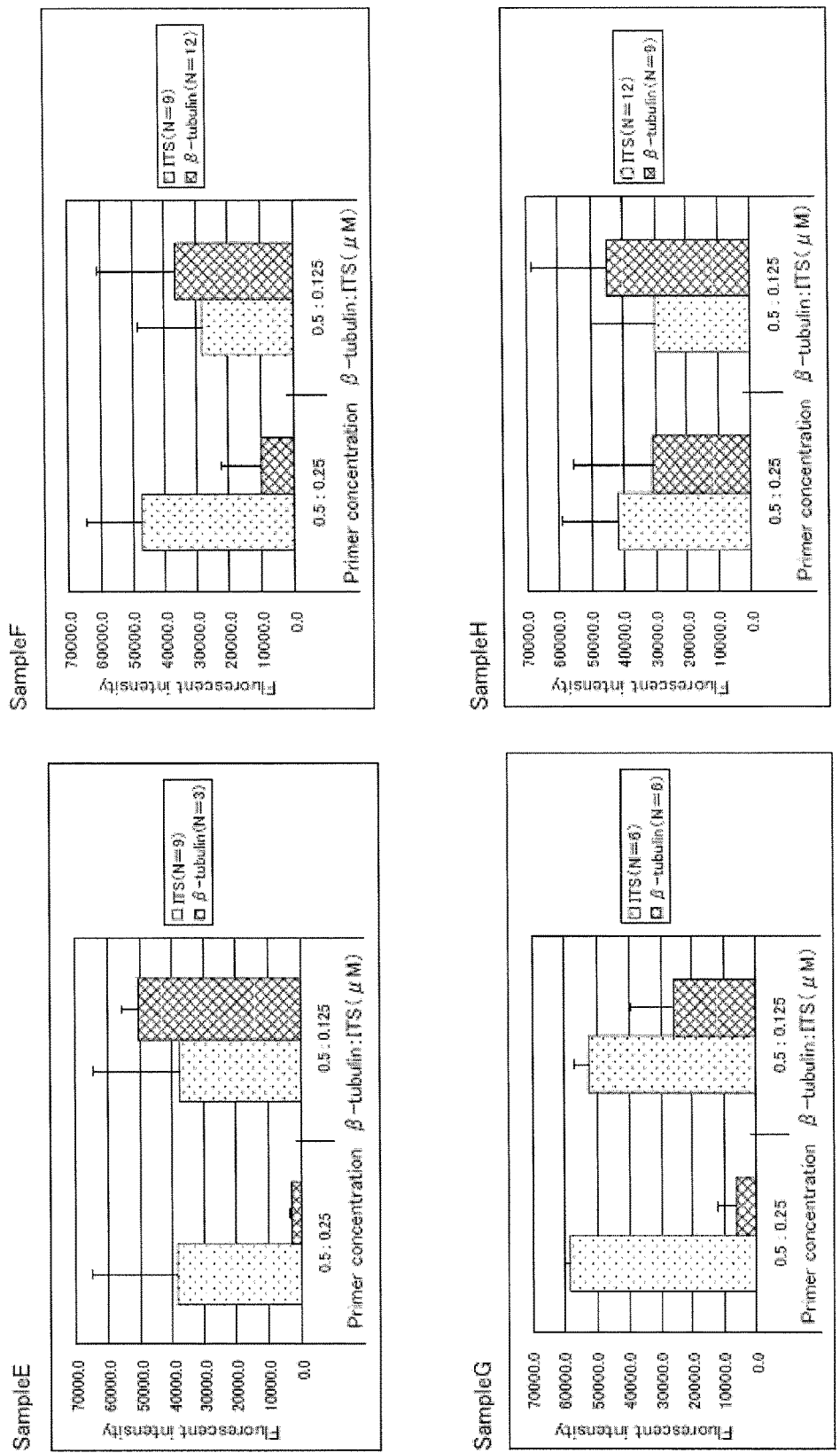
FIG. 14 is a view showing the results of test 3 for finding the primer set concentration capable of detecting both the ITS region and the β-tubulin gene in the simultaneous reaction system, according to one or more embodiments of the present invention.

As the DNA chip, of the probes shown in FIG. 3, one to which the following probes were immobilized was used. Other configurations were the same as those for test 1, and the fluorescent intensity in the probe was measured. According to the concentration ratio of the primer set, an average value of the fluorescent intensity in the probe for measuring the ITS region and an average value of the fluorescent intensity in the probe for measuring the β-tubulin gene were calculated. The results are shown in FIG. 14. Meanwhile, the "N" in FIG. 14 indicates the number of probes×frequency of test (×3).

<Probe Selected from the ITS Region>
(1) *Eurotium* sp. sequence No. 6
(2) *Aspergillus penicillioides* sequence No. 9
(8) *Penichillium* sp. sequence No. 29
(11) *Clandosporium* sp. sequence No. 37
(12) Common to fungi sequence No. 40
<Probe Selected from the β-Tubulin Gene>
(1) *Eurotium* sp. sequence No. 8
(2) *Aspergillus penicillioides* sequence No. 12
(4) *Aspergillus Restricti* Section sequence No. 21
(12) Common to fungi sequence No. 41

When referring to Samples E to H in FIG. 14, as compared with the case where the ratio of the final concentration of the primer set for the β-tubulin gene and the final concentration of the primer set for the ITS region is 0.5 μM:0.25 μM (1:1/2), when the ratio of the final concentration of the primer set for the β-tubulin gene and the final concentration of the primer set for the ITS region is 0.5 μM0.125 μM (1:1/4), the fluorescent intensity of the probe for the ITS region and the fluorescent intensity of the probe for the β-tubulin gene were both increased.

Therefore, in order to judge presence or absence of fungi based on the both detection results, it is thought to be optimum that the ratio of the final concentration of the primer set for the β-tubulin gene and the final concentration of the primer set for the ITS region is 0.5 μM:0.125 μM.

(Test 4)

A test was conducted to examine whether fungi other than the wild fungi contained in Samples A to H collected from the facility environment can be detected by the method for detecting fungi according to one or more embodiments of the present invention in which the ITS region and the β-tubulin gene are target regions.

As the fungi to be detected, a mixture of the following four types of strains 1 to 4 were used.
1. *Aspergillus fumigatus* strain No. JCM10253
2. *Fusarium solani* strain No. NBRC5232
3. *Stachybotrys chartarum* strain No. NBRC5369
4. *Cladsoporium sphaerospermum* strain No. JCM11787

The above-mentioned strains were obtained from the following institutions. JCM: RIKEN BRC microbial Engineering Division (Japan Collection of Microorganisms) NBRC: National Institute of Technology and Evaluation Department of Biotechnology Biological Resources Division (NITE Biological Resource Center)

After planting these strains in a culture medium, and cultivation was conducted by allowing it to stand in a dark place at 25° C. for 7 days, the colony of each species was collected all at once, and the genomic DNA of the fungi was extracted in the same manner as in test 1. By the PCR method, the ITS region and the β-tubulin gene were amplified simultaneously in the same manner as in test 1.

At this time, in the same manner as in test 3, two types of the reaction solution for PCR differing in final concentration ratio of the primer set for amplifying the β-tubulin gene and the primer set for amplifying the ITS region; i.e. 0.5 µM:0.25 µM and 0.5 µM:0.125 µM, were prepared. In each reaction solution for PCR, as for the DNA of the sample, 1.0 µl of each of the strains 1 to 4 (the total amount: 4.0 µl) was contained. By using each reaction solution for PCR, the ITS region and the β-tubulin gene of each of fungi were amplified.

As the DNA chip, of the probes shown in FIG. 3, one to which the following probes were immobilized was used.

Figure 15:
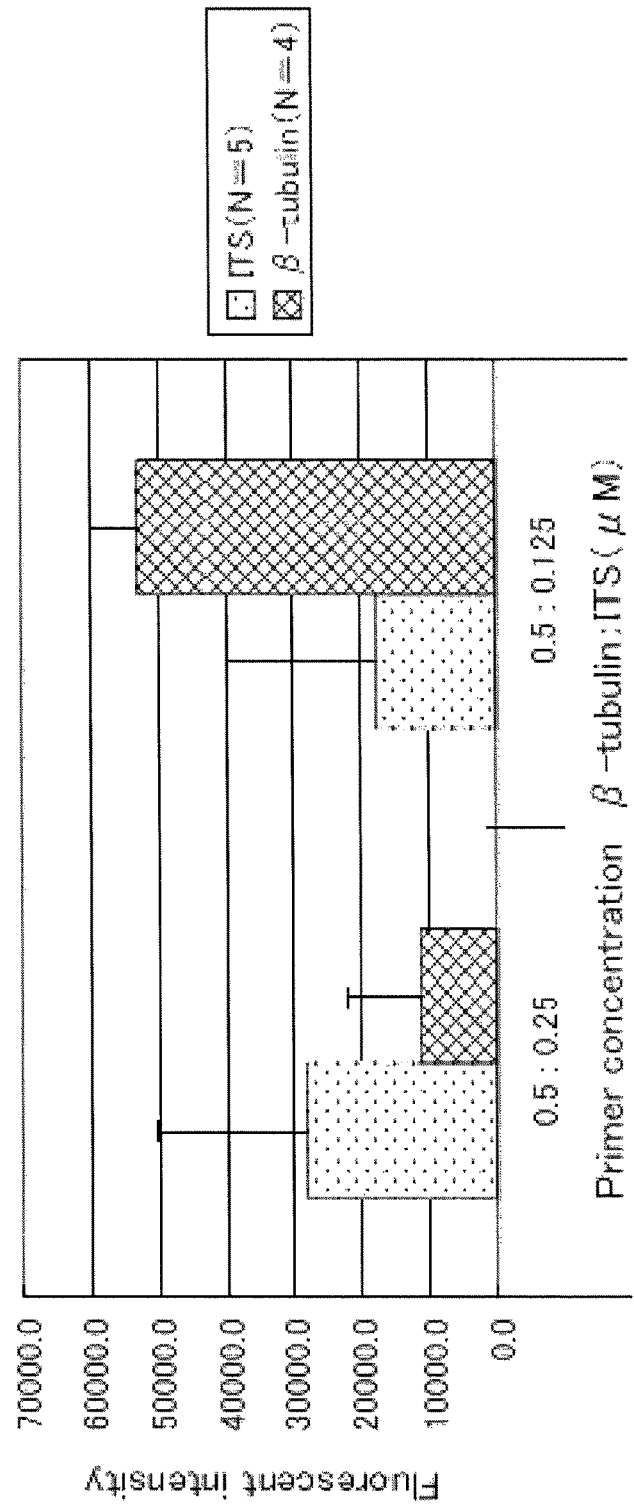
FIG. 15 is a view showing the results of test 4 for confirming whether various fungi which were not contained in samples A to H collected from an environment equipment can be detected by a DNA chip analysis using a multiplex PCR, according to one or more embodiments of the present invention.
Figure 16:
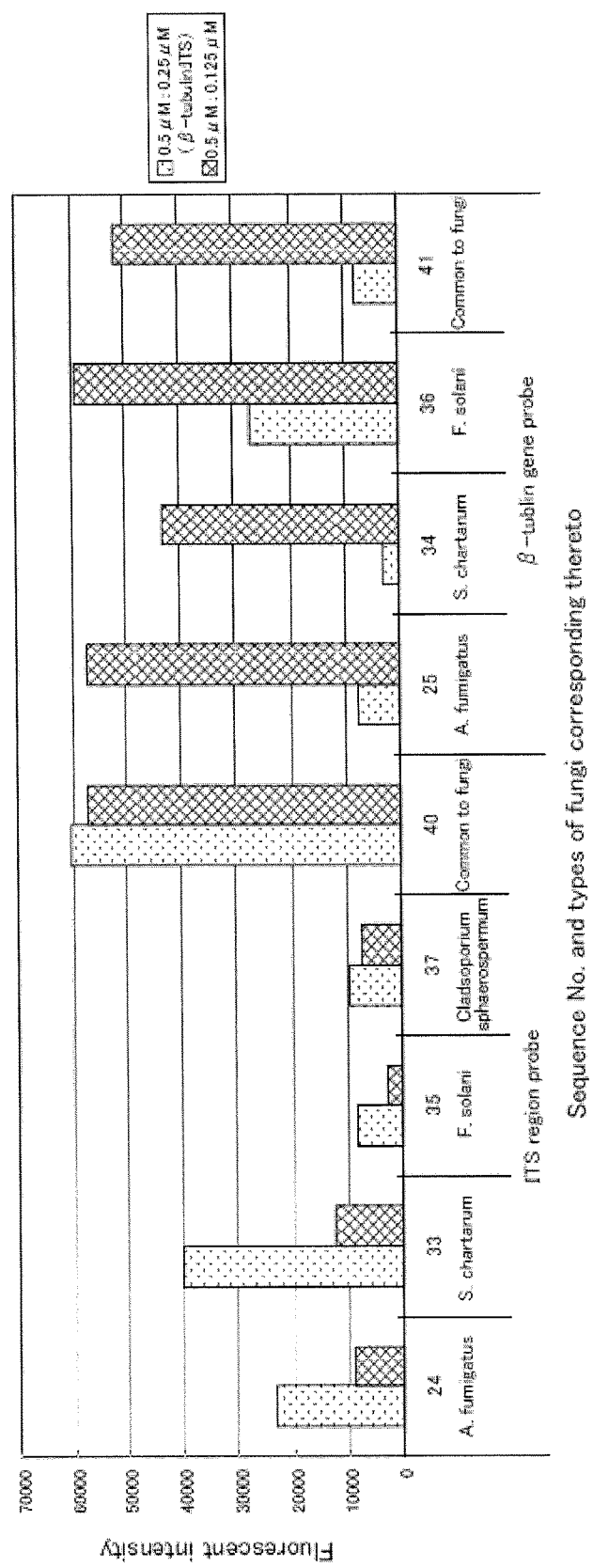
FIG. 16 is a view showing the fluorescent intensity according to the primer set concentration and according to the probe for the sample of experiment 4, according to one or more embodiments of the present invention.

An amplified product by PCR was hybridized to the probe. The fluorescent intensity in the probe was measured. According to the concentration ratio of the primer set, an average value of the fluorescent intensity in the probe for measuring the ITS region and an average value of the fluorescent intensity in the probe for measuring the β-tubulin gene were calculated. As for other points, a test was conducted in the same manner as in test 1. The results are shown in FIG. 15. FIG. 16 shows the concentration ratio of the primer set and the fluorescent intensity according to each probe.

<Probe Selected from the ITS Region>
(6) *Aspergillus Section fumigatus* sequence No. 24
(9) *Stachbotrys chartarum* sequence No. 33
(10) *Fusam solani* sequence No. 35
(11) *Cladsoporium* sp. sequence No. 37
(12) Common to fungi sequence No. 40
<Probe Selected from the β-Tubulin Gene>
(6) *Aspergillus fumigatus* sequence No. 25
(9) *Stachybotrys chartarum* sequence No. 34
(10) *Fusarium solani* sequence No. 36
(12) Common to fungi sequence No. 41

When referring to FIG. 15, in both of the cases, i.e. the case where the ratio of the final concentration of the primer set for the β-tubulin gene and the final concentration of the primer set for the ITS region is 0.5 µM:0.25 µM (1:1/2), when the ratio of the final concentration of the primer set for the β-tubulin gene and the final concentration of the primer set for the ITS region is 0.5 µM:0.125 µM (1:1/4), the fluorescent intensity in the probe for measuring the ITS region and the fluorescent intensity in the probe for measuring the β-tubulin gene were sufficient for detection.

Therefore, as for the above-mentioned four strains 1 to 4, it can be confirmed that they can be detected by the method for detecting fungi of one or more embodiments of the present invention in which the ITS region and the β-tubulin gene are target regions.

Meanwhile, as for *Cladsoporium sphaerospermum*, no fluorescence was detected in the probe for the β-tubulin gene. Then, a method for enabling *Cladsoporium* sp. to be detected was examined, and the following tests 5 and 6 were conducted.

(Test 5)

In test 4, as mentioned above, when the primer set for amplifying the β-tubulin gene (sequence Nos. 3, 4) was used, as for *Cladsoporium sphaerospermum*, no fluorescence was detected in the probe for the β-tubulin gene.

Further, in test 4, a probe which can be complementary connected to the β-tubulin gene is immobilized to the DNA chip, and hence, the reason that no fluorescence was detected in the probe was not clear.

Under such circumstances, a new forward primer for amplifying the β-tubulin gene (sequence No. 5) was designed exclusively for *Cladosporium* sp., and by using a primer set composed of this primer and the above-mentioned reverse primer (sequence No. 4), the β-tubulin gene of *Cladsoporium sphaerospermum* was amplified, and a test was conducted to confirm whether fluorescence is detected in the probe for the β-tubulin gene.

As the fungi to be detected, a mixture of the four types of strains 1 to 4 which were the same as those in test 4 was used.

Further, as the reaction solution for PCR, two types of the reaction solution for PCR differing in final concentration ratio of the primer set for amplifying the β-tubulin gene and the primer set for amplifying the ITS region; i.e. 0.5 µM:0.25 µM and 0.5 µM:0.125 µM, were prepared. For each of these solutions, the forward primer for amplifying the β-tubulin gene exclusively for *Cladosporium* sp. was added such the final concentration thereof become 0 µM, 0.5 µM, 0.25 WI and 0.125 µM, whereby 8 types of a reaction solution for PCR were prepared.

Specifically, Ampdirect® (manufactured by Shimadzu Corporation) was used, 20 µl of a reaction solution having the following composition was prepared, and in the same manner as in test 1, the ITS region and the β-tubulin gene of each of fungi were amplified.
1. Ampdirect (G/Crich) 4.0 µl
2. Ampdirect (addition-4) 4.0 µl
3. dNTPmix 1.0 µl
4. Cy-5dCTP 0.2 µl
5. ITS1-Fw primer (5 µM, 2.5 µM) 0.5 µl, 0.25 µl
6. ITS1-Rv primer (5 µM, 2.5 µM) 0.5 µl, 0.25 µl
7. BtF primer (10 µM) 1.0 µl
8. BtR primer (10 µM) 1.0 µl
9. ClaS-beta2 (0 µM, 10 µM, 5 µM, 2.5 µM) 0 µl, 1.0 µl, 0.5 µl, 0.25 µl
10. Template DNA (strains 1 to 4, each 1.0 µl) 4.0 µl
11. NovaTaq polymerase 0.2 µl
12. Water (added until the total volume became 20.0 µl)

As the DNA chip, of the probes shown in FIG. 3, one to which the probe (sequence No. 39) specific to *Cladosporium sphaerospermum* alone was fixed was used. Other points were the same as those in test 1. An amplified product by PCR was hybridized with the probe, and the fluorescence in the probe was measured. The results are shown in FIG. 17.

Figure 17:
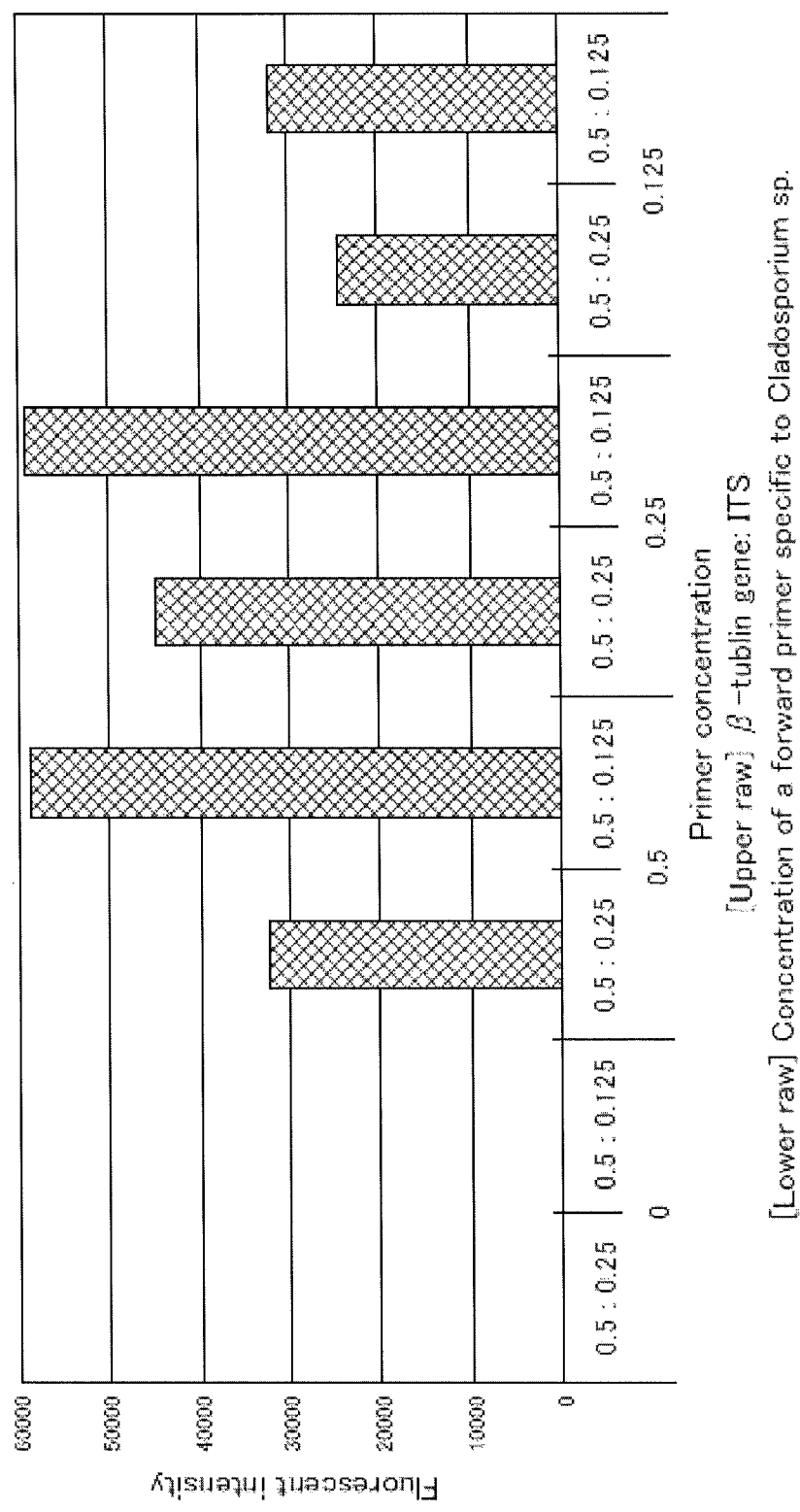
FIG. 17 is a view showing the results of test 5 for confirming whether *Cladosporium* sp. can be detected by a DNA chip using a multiplex PCR, according to one or more embodiments of the present invention.

As shown in FIG. 17, it has been revealed that, when the ratio of the final concentration of the primer set for measuring the β-tubulin gene and the final concentration of the primer set for measuring the ITS region is in the range of 0.5 µM:0.25 µM (1:1/2) to 0.5 µM:0.125 µM (1:1/4), and, in particular, when the final concentration of the forward primer exclusively for *Cladosporium* sp. is 0.5 µM to 0.25 µM, a high fluorescent intensity could be obtained for *Cladosporium* sp.

(Test 6)

An examination was made on the effects exerted by the forward primer (sequence No. 5) exclusive for the *Cladosporium* sp. used in test 5 on the fluorescent intensity in the probe other than the probe (sequence No. 39) specific to *Cladosporium* sp.

As the fungi to be detected, a mixture of the four types of strains 1 to 4 as those in test 4 was used.

Further, as the reaction solution for PCR, a reaction solution for PCR in which the final concentration ratio of the primer set for amplifying the β-tubulin gene and the primer set for amplifying the ITS region was 0.5 µM:0.125 µM was prepared, and the forward primer for amplifying the β-tubulin gene exclusively for *Cladosporium* sp. was added such that the final concentration thereof became 0 µM, 0.5 µM and 0.25 µM, whereby 3 types of the solution for PCR were prepared.

Specifically, Ampdirect® (manufactured by Shimadzu Corporation) was used, 20 µl of a reaction solution having the following composition was prepared, and in the same manner as in test 1, the ITS region and the β-tubulin gene of each of fungi were amplified.
1. Ampdirect (G/Crich) 4.0 µl
2. Ampdirect (addition-4) 4.0 µl
3. dNTPmix 1.0 µl
4. Cy-5dCTP 0.2 µl
5. ITS1-Fw primer (2.5 µM) 0.25 µl
6. ITS1-Rv primer (2.5 µM) 0.25 µl
7. BtF primer (10 µM) 1.0 µl
8. BtR primer (10 µM) 1.0 µl
9. ClaS-beta2 (0 µM, 10 µM, 5 µM) 0 µl, 1.0 µl, 0.5 µl
10. Template DNA (strains 1 to 4, each 1.0 µl) 4.0 µl
11. NovaTaq polymerase 0.2 µl
12. Water (added until the total volume became 20.0 µl)

As the DNA chip, of the probes shown in FIG. 3, one to which the probes of the same strains 1 to 4 as in test 4 were immobilized was used. The other points are the same as in test 1, and an amplified product by PCR was hybridized to a probe.

Then, the fluorescent intensity in each probe was measured, and according to the forward primer for amplifying the β-tubulin gene the average value of the fluorescent intensity in the probe for the ITS region and the fluorescent intensity in the probe for the β-tubulin gene exclusive for *Cladosporium* sp. was calculated. The results are shown in FIG. 18.

Figure 18:
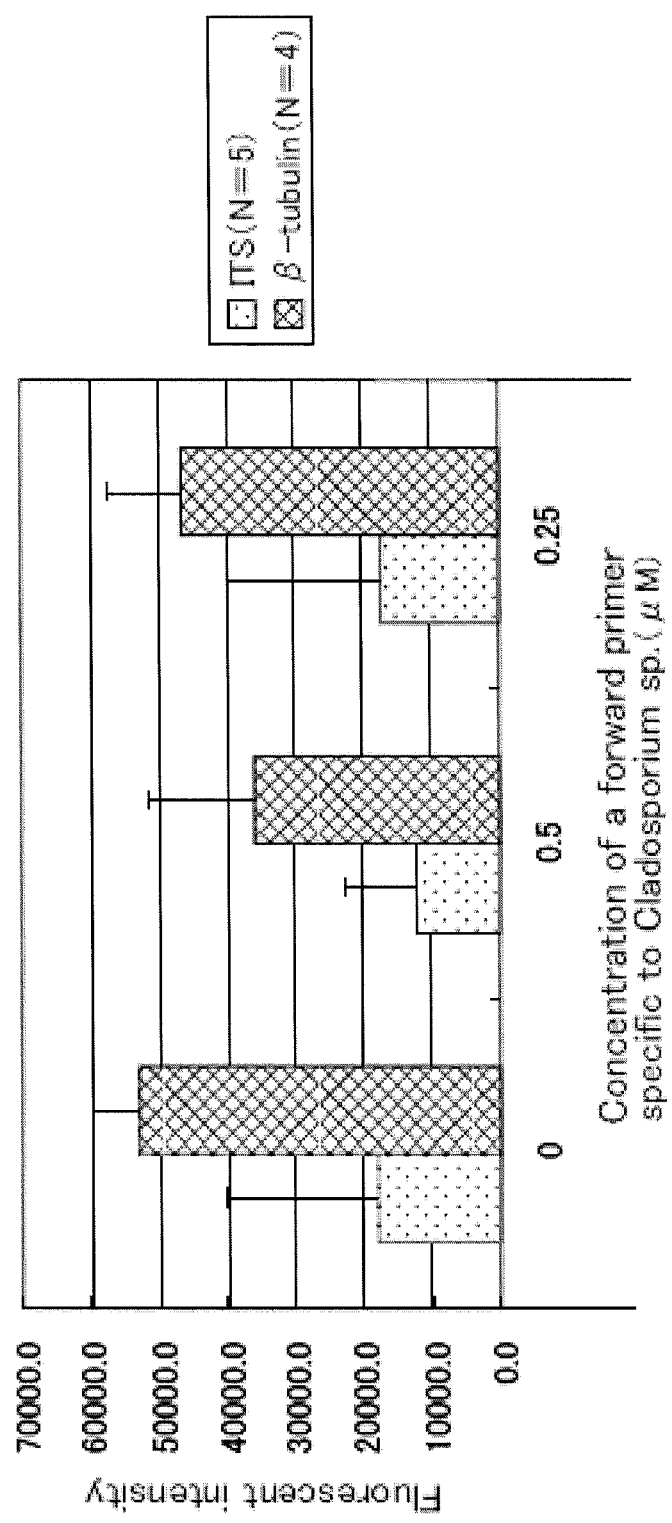
FIG. 18 is a view showing the results of test 6 for confirming the effects exerted by the addition of a forward primer specific to *Cladosporium* sp. to a reaction solution for PCR on other types of fungi, according to one or more embodiments of the present invention.

As shown in FIG. 18, by adding a forward primer for amplifying the β-tubulin gene exclusive for *Cladosporium* sp. to a reaction solution for multiplex PCR, the fluorescent intensity in the probe selected from the β-tubulin gene other than the probe specific to *Cladosporium* sp. was lowered. The degree of lowering in fluorescent intensity was smaller in the case of the probe of which the concentration of the forward primer for amplifying the β-tubulin gene exclusive for *Cladosporium* sp. was 0.25 µM as compared with the concentration of the forward primer was 0.5 µM. Accordingly, it has been revealed that a concentration of the forward primer for amplifying the β-tubulin gene of 0.25 µM was appropriate.

Next, the results of a test for detecting fungi according to the method for detecting fungi of one or more embodiments of the present invention will be explained in detail.

(Test 7: Cultivation Test According to Water Activity Value of the Composition of Various Culture Mediums)

To a PDA (Potato Dextrose Agar) medium and a MY (Malt+Yeast) medium, sugar or the like were added to prepare various culture mediums showing various water activity values. In these culture mediums, xerophilic fungi, xerophilous fungi and hygrophilous fungi were cultivated, and the results of incubation were evaluated.

1. Method for Preparing a Culture Medium
(1) PDA Culture Medium

To PDA (manufactured by DIFCO Laboratories), glucose (manufactured by Wako Pure Chemical Industries, Ltd.) and sucrose (manufactured by Wako Pure Chemical Industries, Ltd.) were added in various amount ratios, and the resulting mixture was suspended in 1 l of ion exchange water. Then, the suspension was then molten in an autoclave, and dispensed in petri dish. Before dispensing in petri dish, in order to suppress proliferation of bacterium, Chloramphenicol (manufactured by Wako Pure Chemical Industries, Ltd.) was added such that the final concentration thereof became 50 ppm. The same applies to the MY culture medium.

(2) MY Culture Medium

To the following MY, at least any of sucrose (Wako Pure Chemical Industries, Inc.), glucose, agar (Wako Pure Chemical Industries, Inc.) and glycerin were added at various ratios, and the resultant was suspended in ion exchange water of 100 ml, molten in an autoclave and dispensed in petri dish.

MY: malt (Malt Extract, manufactured by DIFCO Laboratories)+Yeast (Yeast Extract, manufactured by DIFCO Laboratories)

2. Measurement of Water Activity Value of Culture Medium

For a prescribed amount of the culture medium which was actually used in cultivation, the water activity value thereof was measured in a dedicated sealed container by using a Rotronic water activity measurement apparatus (manufactured by GSI Creos Corporation).

3. Evaluation of Cultivation

By using various culture mediums prepared by the above-mentioned method (Examples 1 to 10 of FIG. 19 and Referential Examples 1 to 6), xerophilic fungi (*Eurotium herbariorum*), xerophilous fungi (*A. niger*) and hygrophilous fungi (*Fusarium* sp.) were cultivated in a dark place at 25° C. for 72 hours, and the diameter of the resulting colony was measured. A colony having a diameter of 10 mm or more was expressed as ○ and a colony having a diameter of less than 10 mm was expressed as x. The results are shown in FIG. 19.

As shown in the figure, it can be understood that, when various culture mediums in Examples 1 to 10 were used, any of xerophilic fungi, xerophilous fungi and hygrophilous fungi were fully proliferated. On the other hand, it can also be understood that, when culture mediums in Referential Examples 1 to 6 were used, there were types of fungi which were not proliferated sufficiently. Therefore, when a plurality of types of fungi are cultivated simultaneously, the water activity value may be less than 1.0 and 0.90 or more and the sugar concentration be 5% to 50%.

(Test 8: Cultivation Test by Various Culture Mediums)

By using six types of culture mediums of Referential Examples 1, 2 and 4 to 6 and Example 7, shown in FIG. 19, various types of fungi were cultivated at 25° C. in a dark place for 168 hours, and the diameter of the resulting colony was measured.

As the types of fungi to be tested, the following 14 types were used. The results are shown in FIG. 20. Of them, the types 1 to 4 are xerophilic fungi, the types 5 to 10 are xerophilous fungi and the types 11 to 14 are hygrophilous fungi. Meanwhile, these types of fungi to be tested were obtained by collecting from the environment, followed by identification. These numbers are added just for convenience.
1. *Aspergillus penicillioides*, K-7-4
2. *Aspergillus restrictus*, I-2-1
3. *Eurotium herbariorum*, b2-1
4. *Wallemia sebi*, KSS-1127
5. *Aspergillus flavus*, B-3-3)
6. *Aspergillus fumigatus*, KSS-1126
7. *Aspergillus niger* A-1-1
8. *Aspergillus versicolor*, b3-1)
9. *Penicillium glabrum*, B-4-3
10. *Penicullum rugulosum*, E-2-3)
11. *Cladosporium. sphaerospermum*, I-4-2
12. *C.cladosporioides*, A-2-1
13. *Fusarium* sp., B5-3-C
14. *Stachybotrys* sp., KSS-1125

As shown in FIG. 20, in the culture medium (M40Y) of Example 7, colonies of a plurality of types of fungi differing in humidity suited to growth were generated. It can be understood that all of the above-mentioned types of fungi 1 to 14 were sufficiently proliferated.

As mentioned above, it can be understood, by using the culture medium of Example 7, a plurality of fungi 1 to 14 differing in properties regarding the optimum humidity can be cultivated simultaneously in the same culture medium.

(Test 9: Cultivation Test at Various Temperatures)

Figure 22:
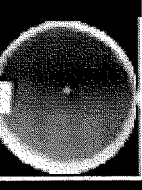
FIG. 22 is a view showing a photograph of a colony when xerophilic fungi, xerophilous fungi and hygrophilous fungi are cultivated at various temperatures, according to one or more embodiments of the present invention.

By using the M40Y culture medium used in Example 7, cultivation was conducted at various temperatures, and the diameter of the resulting colony was measured. As the types of fungi to be tested, as in test 1, the 14 types of fungi including xerophilic fungi, xerophilous fungi and hygrophilous fungi were used, and cultivation was conducted in a dark place for 168 hours. The results are shown in FIG. 21. As for the types of fungi 3, 8 and 13, the photographs of their colonies are shown in FIG. 22.

As shown in Examples 11 to 13 of FIG. 21, in a cultivation temperature range of 23° C. to 27° C., it can be understood that any of xerophilic fungi, xerophilous fungi and hygrophilous fungi were sufficiently proliferated. On the other hand, as shown in Referential Examples 7 to 9, in a cultivation temperature range of 30° C. to 35° C., some types of fungi cannot grow. Therefore, in order to cultivate a plurality of types of types of fungi simultaneously, a cultivation temperature of 25° C.±2° C. may be used.

(Test 10: DNA Chip Analysis Test)

Various fungi were cultivated by using the M40Y culture medium used in Example 7, the resulting colonies were mixed, and genomic DNA was extracted all at once. The ITS1 region was amplified by the PCR method, and an examination was conducted by means of a DNA chip whether the fungi to be detected were included in an amplified product. Further, in order to verify the results of an examination by means of a DNA chip, a DNA sequence analysis was conducted. Specifically, the analysis was conducted as follows.

First, as a sample using the M40Y medium used in Example 7, 60 samples from No. 1 to No. 60 were prepared. Next, by using an air sampler, air was collected from the general environment, and the air was blown to each of the above-mentioned samples for cultivation. Cultivation was conducted by allowing the sample to stand in a dark place of 25° C. for 7 days.

Next, for each sample, in order to subject various colonies generated in a culture medium to a DNA sequence analysis, parts of colonies were collected separately and cultivated separately in a dark place at 25° C. for 7 to 10 days.

For each sample, colonies of various types of fungi generated in the culture medium were placed in a vial filled with φ0.5 mm zirconia beads. The vial was immersed in liquid nitrogen to allow the sample to be frozen, and the cells of the fungi were crushed by means of a shaker.

Subsequently, for each sample, genomic DNA of fungi was extracted by a DNA extraction apparatus, and the ITS region of each of fungi was amplified by the PCR method.

Specifically, Ampdirect® (manufactured by Shimadzu Corporation) was used as the reaction solution for PCR, 20 μl of a reaction solution having the following composition was prepared.
1. Ampdirect addition (G/Crich) 4.0 μl
2. Ampdirect (addition-4) 4.0 μl
3. dNTPmixture 1.0 μl
4. Cy5-dCTP 0.2 μl
5. Forward primer for amplifying the ITS1 region (10 μl M, sequence No. 42, synthesized by Sigma-Aldrich) 1.0 μl
6. Reverse primer for amplifying the ITS1 region (10 μM, sequence No. 43, synthesized by Sigma-Aldrich) 1.0 μl
7. Genomic DNA 1.0 μl
8. NovaTaq polymerase 0.2 μl
9. Water (added until the total amount became 20.0 μl)

By using this reaction solution for PCR, by means of a nucleic acid amplification apparatus (TaKaRa PCR Thermal Cycler Dice® Gradient, manufactured by Takara Bio Inc.), amplification of DNA was conducted under the following conditions:
1. 95° C. for 10 minutes
2. 95° C. for 30 seconds
3. 56° C. for 30 seconds
4. 72° C. for 60 seconds (2 to 4 were repeated 40 cycles)
5. 72° C. for 10 minutes As the DNA chip, gene Silicon®, (manufactured by Toyo Kohan Co., Ltd.) was used in which probes comprising base sequences shown in sequence No. 44, sequence No. 45 and sequence No. 46 were immobilized. They were a probe for detecting *Aspergillus vitricola*, a probe for detecting *Aspergillus penicillioides*, and a probe for detecting *Eurotium* sp., respectively.

Subsequently, a PCR amplified product was mixed with a buffer (3×SSC citric acid–physiological saline+0.3% SDS), and the resultant mixture was added dropwise to the DNA chip.

This DNA chip was allowed to stand at 45° C. for 1 hour. By using the above-mentioned buffer, a PCR amplified product was washed away from the DNA chip.

Subsequently, the DNA chip was mounted in a label detection apparatus (BIOSHOT, a scanner exclusive for gene silicon, manufactured by Toyo Kohan Co., Ltd.), and the fluorescent intensity in each probe was measured.

The results are shown in FIGS. 23 to 25.

Further, in order to conduct DNA sequence analysis of the types of fungi contained in each sample, the genomic DNA was extracted from the types of fungi obtained by cultivating separately according to the colony as mentioned above, and an amplified product was obtained by the PCR method.

At this time, as the primer set, one comprising base sequences shown in sequence Nos. 42 and 43 were used, and as the nucleic acid synthetase, TAKARA ExTaq polymerase was used. Further, as the nucleic acid amplification apparatus, TaKaRa PCR Thermal Cycler Dice® Gradient (manufactured by manufactured by Takara Bio Inc.), a PCR reaction was conducted, with the other points being the same as mentioned above.

By using an amplified product obtained by this PCR reaction and the primer set comprising the base sequences shown in the sequence Nos. 47 and 48 as a primer for sequence analysis, the DNA sequence analysis was entrusted to Takara Bio Inc., and the sequence analysis of the ITS1 region was conducted by a DNA sequencer. As a result, as shown in FIGS. 23 to 25, four types of fungi were confirmed in each sample, at most.

In the "DNA chip analysis (probe fluorescent intensity)" shown in FIGS. 23 to 25, a part which was thought to be positive was surrounded by a thick-bordered box. In these boxes, as for the "strain contained in a sample confirmed by the ITS sequence analysis", the same types of fungi are indicated.

As for Sample No. 3 in which the presence of xerophious fungi (*Penicillium* sp.) and hygrophilous fungi (*Cladosporium* sp.) was confirmed by the ITS analysis, by using a DNA chip to which a probe for detecting *Penicillium* sp. and a probe for detecting *Cladosporium* sp. were fixed, in the same manner as mentioned above, the fluorescent intensity was measured by means of a label detection apparatus. As a result, the presence of these types of fungi (*Penicillium* sp., *Cladosporium* sp.) was confirmed.

Accordingly, it has been revealed that, by the method for detecting fungi of one or more embodiments of the present invention, when a plurality of types of fungi are cultivated simultaneously in the same culture medium, each of fungi can be specifically detected.

The present invention is not restricted to the above-mentioned embodiments or examples, and various modifications can be possible within the scope of the present invention.

For example, the components other than those for the primer set for amplifying the ITS region and those for the primer set for amplifying the β-tubulin gene can be appropriately modified. Further, in a method in which an object fungi are detected by using these amplified products, in addition to detection by fluorescence by using a DNA chip as mentioned above, an amplified product can be detected by electrophoresis or by using a current-detection type DNA chip.

In the above-mentioned Examples, M40Y or the like are used as the culture medium. The type of the culture medium is not limited to this, and can be changed appropriately. For example, another solid culture medium having a water activity value of less than 1.0 and 0.90 or more and a sugar concentration of 5% to 50% can be used.

INDUSTRIAL APPLICABILITY

One or more embodiments of the present invention can be used when a plurality of types of fungi are detected specifically and in a multiple way in an environmental inspection, a food inspection, an epidemiological environmental examination, clinical trials, animal hygiene or the like. Further, one or more embodiments of the present invention can be used for fungi inspection in food manufacturing sites, clinical sites, environments for protecting cultural assets or the like.

The invention claimed is:

1. A method for detecting fungi comprising:
preparing a PCR reaction solution comprising genomic DNA from collected fungi, a primer set for amplifying target regions of β-tubulin genes, and a primer set for amplifying target regions of ITS regions;
wherein, in the PCR reaction solution, the concentration ratio of the primer set for amplifying the target regions of the β-tubulin genes to the primer set for amplifying the target regions of the ITS regions is 1:0.5 to 1:0.25,
amplifying DNA fragments from the collected fungi by a multiplex PCR in the PCR reaction solution that includes a label,
hybridizing the labeled amplification products from the multiplex PCR to a DNA chip in which a plurality of probes selected from DNA of fungi to be detected are fixed; and
detecting the presence of fungi by measuring the combined label intensities of the labeled amplification product of the ITS region and the labeled amplification product of the β-tubulin gene hybridized on the DNA chip.

2. The method for detecting fungi according to claim 1, wherein the label is a fluorescent label.

3. The method for detecting fungi according to claim 1, wherein, in the PCR reaction solution, the primer set for amplifying the target regions of the ITS regions is a primer set comprising a forward primer comprising a base sequence represented by SEQ ID NO:1 and a reverse primer comprising a base sequence represented by SEQ ID NO:2, and the primer set for amplifying the target regions of the β-tubulin genes is a primer set comprising a forward primer comprising a base sequence represented by SEQ ID NO:3 and a reverse primer comprising a base sequence represented by SEQ ID NO:4.

4. The method for detecting fungi according to claim 3, wherein, in the PCR reaction solution, a primer comprising a base sequence represented by sequence No. 5 is further used as a forward primer.

* * * * *

SEQUENCE LISTING

<160> NUMBER OF SEQ ID NOS: 48

<210> SEQ ID NO 1
<211> LENGTH: 26
<212> TYPE: DNA
<213> ORGANISM: Artificial
<220> FEATURE:
<223> OTHER INFORMATION: synthetic DNA

<400> SEQUENCE: 1
ttggtcattt agaggaagta aaagtc                                          26

<210> SEQ ID NO 2
<211> LENGTH: 19
<212> TYPE: DNA
<213> ORGANISM: Artificial
<220> FEATURE:
<223> OTHER INFORMATION: synthetic DNA

<400> SEQUENCE: 2
ctgcgttctt catcgatgc                                                  19

<210> SEQ ID NO 3
<211> LENGTH: 24
<212> TYPE: DNA
<213> ORGANISM: Artificial
<220> FEATURE:
<223> OTHER INFORMATION: synthetic DNA

<400> SEQUENCE: 3
ggtaaccaaa tcggtgctgc tttc                                            24

<210> SEQ ID NO 4
<211> LENGTH: 24

```
<212> TYPE: DNA
<213> ORGANISM: Artificial
<220> FEATURE:
<223> OTHER INFORMATION: synthetic DNA

<400> SEQUENCE: 4
accctcagtg tagtgaccct tggc                                            24

<210> SEQ ID NO 5
<211> LENGTH: 21
<212> TYPE: DNA
<213> ORGANISM: Artificial
<220> FEATURE:
<223> OTHER INFORMATION: synthetic DNA

<400> SEQUENCE: 5
aagtgaactt tcaggcaccc g                                               21

<210> SEQ ID NO 6
<211> LENGTH: 23
<212> TYPE: DNA
<213> ORGANISM: Eurotium sp.

<400> SEQUENCE: 6
gtctgagttt ttagttaaac aat                                             23

<210> SEQ ID NO 7
<211> LENGTH: 20
<212> TYPE: DNA
<213> ORGANISM: Eurotium sp.

<400> SEQUENCE: 7
gaagactaac atttgaacac                                                 20

<210> SEQ ID NO 8
<211> LENGTH: 23
<212> TYPE: DNA
<213> ORGANISM: Eurotium sp.

<400> SEQUENCE: 8
aggcctccaa caacaaatat gtc                                             23

<210> SEQ ID NO 9
<211> LENGTH: 21
<212> TYPE: DNA
<213> ORGANISM: Aspergillus penicillioides

<400> SEQUENCE: 9
gagacctcaa ccatgaacac t                                               21

<210> SEQ ID NO 10
<211> LENGTH: 22
<212> TYPE: DNA
<213> ORGANISM: Aspergillus penicillioides

<400> SEQUENCE: 10
gagacctcaa ccattgaaca ct                                              22

<210> SEQ ID NO 11
<211> LENGTH: 22
<212> TYPE: DNA
<213> ORGANISM: Aspergillus penicillioides

<400> SEQUENCE: 11
```

```
gagacctctc aaccattgaa ca                                              22

<210> SEQ ID NO 12
<211> LENGTH: 22
<212> TYPE: DNA
<213> ORGANISM: Aspergillus penicillioides

<400> SEQUENCE: 12
catcgtcagc atgtcacacc gc                                              22

<210> SEQ ID NO 13
<211> LENGTH: 25
<212> TYPE: DNA
<213> ORGANISM: Aspergillus vitricola

<400> SEQUENCE: 13
ctgagttttc ataaaagaaa aatcg                                           25

<210> SEQ ID NO 14
<211> LENGTH: 24
<212> TYPE: DNA
<213> ORGANISM: Aspergillus vitricola

<400> SEQUENCE: 14
ctgagttttc ataaagaaaa attg                                            24

<210> SEQ ID NO 15
<211> LENGTH: 24
<212> TYPE: DNA
<213> ORGANISM: Aspergillus vitricola

<400> SEQUENCE: 15
ccaaagtcca attggcatca aact                                            24

<210> SEQ ID NO 16
<211> LENGTH: 23
<212> TYPE: DNA
<213> ORGANISM: Aspergillus Section Restricti

<400> SEQUENCE: 16
gagttttcat ataagaaaaa tcg                                             23

<210> SEQ ID NO 17
<211> LENGTH: 27
<212> TYPE: DNA
<213> ORGANISM: Aspergillus Section Restricti

<400> SEQUENCE: 17
ttgccgtctg agttgtcata tacgaaa                                         27

<210> SEQ ID NO 18
<211> LENGTH: 22
<212> TYPE: DNA
<213> ORGANISM: Aspergillus Section Restricti

<400> SEQUENCE: 18
ccggagactc caacattgaa ca                                              22

<210> SEQ ID NO 19
<211> LENGTH: 25
<212> TYPE: DNA
<213> ORGANISM: Aspergillus Section Restricti

<400> SEQUENCE: 19
```

```
gtctgagttt tcatatacga aaaat                                          25

<210> SEQ ID NO 20
<211> LENGTH: 23
<212> TYPE: DNA
<213> ORGANISM: Aspergillus Section Restricti

<400> SEQUENCE: 20
ctgagttttc atatacgaaa aat                                            23

<210> SEQ ID NO 21
<211> LENGTH: 21
<212> TYPE: DNA
<213> ORGANISM: Aspergillus Section Restricti

<400> SEQUENCE: 21
atcaattagt atgccacgca c                                              21

<210> SEQ ID NO 22
<211> LENGTH: 25
<212> TYPE: DNA
<213> ORGANISM: Aspergillus Section Nidulantes

<400> SEQUENCE: 22
actactgaac ttcatgcctg agagt                                          25

<210> SEQ ID NO 23
<211> LENGTH: 22
<212> TYPE: DNA
<213> ORGANISM: Aspergillus Section Nidulantes

<400> SEQUENCE: 23
tttgatcgag tcttggacgg gt                                             22

<210> SEQ ID NO 24
<211> LENGTH: 20
<212> TYPE: DNA
<213> ORGANISM: Aspergillus Section Fumigati

<400> SEQUENCE: 24
gaacgctgtt ctgaaagtat                                                20

<210> SEQ ID NO 25
<211> LENGTH: 21
<212> TYPE: DNA
<213> ORGANISM: Aspergillus Section Fumigati

<400> SEQUENCE: 25
aacatctcac gatctgactc g                                              21

<210> SEQ ID NO 26
<211> LENGTH: 21
<212> TYPE: DNA
<213> ORGANISM: Aspergillus Section Flavi

<400> SEQUENCE: 26
gcaactaagg tacagtaaac a                                              21

<210> SEQ ID NO 27
<211> LENGTH: 20
<212> TYPE: DNA
<213> ORGANISM: Aspergillus Section Flavi
```

<400> SEQUENCE: 27
tgaaaacgct ttgcaactcc                                               20

<210> SEQ ID NO 28
<211> LENGTH: 27
<212> TYPE: DNA
<213> ORGANISM: Penicillium sp.

<400> SEQUENCE: 28
agtctgagtg aaaatataaa ttattta                                       27

<210> SEQ ID NO 29
<211> LENGTH: 22
<212> TYPE: DNA
<213> ORGANISM: Penicillium sp.

<400> SEQUENCE: 29
ttgcagtctg agcgaaaacg ca                                            22

<210> SEQ ID NO 30
<211> LENGTH: 21
<212> TYPE: DNA
<213> ORGANISM: Penicillium sp.

<400> SEQUENCE: 30
tgtcaattga tacccaacgc g                                             21

<210> SEQ ID NO 31
<211> LENGTH: 20
<212> TYPE: DNA
<213> ORGANISM: Penicillium sp.

<400> SEQUENCE: 31
gatctttcag gatttgcagc                                               20

<210> SEQ ID NO 32
<211> LENGTH: 22
<212> TYPE: DNA
<213> ORGANISM: Penicillium sp.

<400> SEQUENCE: 32
gtataaaggc ttctctaatg tt                                            22

<210> SEQ ID NO 33
<211> LENGTH: 26
<212> TYPE: DNA
<213> ORGANISM: Stachybotrys chartarum

<400> SEQUENCE: 33
accccaaact cttgtgtttt tttcag                                        26

<210> SEQ ID NO 34
<211> LENGTH: 20
<212> TYPE: DNA
<213> ORGANISM: Stachybotrys chartarum

<400> SEQUENCE: 34
ctcggctcac aatttcccca                                               20

<210> SEQ ID NO 35
<211> LENGTH: 23
<212> TYPE: DNA
<213> ORGANISM: Fusarium solani

<400> SEQUENCE: 35
ctgagtaaaa caagcaaata aat                                              23

<210> SEQ ID NO 36
<211> LENGTH: 22
<212> TYPE: DNA
<213> ORGANISM: Fusarium solani

<400> SEQUENCE: 36
tagatttggt ataggcttcg gg                                               22

<210> SEQ ID NO 37
<211> LENGTH: 23
<212> TYPE: DNA
<213> ORGANISM: Cladosporium sp.

<400> SEQUENCE: 37
actcttgcgt aactttgcag tct                                              23

<210> SEQ ID NO 38
<211> LENGTH: 25
<212> TYPE: DNA
<213> ORGANISM: Cladosporium sp.

<400> SEQUENCE: 38
ggtgttgtca gtgtgtggac gtgga                                            25

<210> SEQ ID NO 39
<211> LENGTH: 20
<212> TYPE: DNA
<213> ORGANISM: Cladosporium sp.

<400> SEQUENCE: 39
tgaggctctt gggacgtgcg                                                  20

<210> SEQ ID NO 40
<211> LENGTH: 19
<212> TYPE: DNA
<213> ORGANISM: Artificial
<220> FEATURE:
<223> OTHER INFORMATION: synthetic DNA

<400> SEQUENCE: 40
gcatcgatga agaacgcag                                                   19

<210> SEQ ID NO 41
<211> LENGTH: 20
<212> TYPE: DNA
<213> ORGANISM: Artificial
<220> FEATURE:
<223> OTHER INFORMATION: synthetic DNA

<400> SEQUENCE: 41
gagcccggta ccatggacgc                                                  20

<210> SEQ ID NO 42
<211> LENGTH: 26
<212> TYPE: DNA
<213> ORGANISM: Aspergillus sp., Eurotium sp.

<400> SEQUENCE: 42
ttggtcattt agaggaagta aaagtc                                           26

```
<210> SEQ ID NO 43
<211> LENGTH: 19
<212> TYPE: DNA
<213> ORGANISM: Aspergillus sp., Eurotium sp.

<400> SEQUENCE: 43
ctgcgttctt catcgatgc                                                19

<210> SEQ ID NO 44
<211> LENGTH: 24
<212> TYPE: DNA
<213> ORGANISM: Aspergillus vitricola

<400> SEQUENCE: 44
ctgagttttc ataaagaaaa attg                                          24

<210> SEQ ID NO 45
<211> LENGTH: 21
<212> TYPE: DNA
<213> ORGANISM: Aspergillus penicillioides

<400> SEQUENCE: 45
gagacctcaa ccatgaacac t                                             21

<210> SEQ ID NO 46
<211> LENGTH: 20
<212> TYPE: DNA
<213> ORGANISM: Eurotium sp.

<400> SEQUENCE: 46
gaagactaac atttgaacac                                               20

<210> SEQ ID NO 47
<211> LENGTH: 19
<212> TYPE: DNA
<213> ORGANISM: Penicillium sp., Cladosporium sp.

<400> SEQUENCE: 47
tccgtaggtg aacctgcgg                                                19

<210> SEQ ID NO 48
<211> LENGTH: 20
<212> TYPE: DNA
<213> ORGANISM: Penicillium sp., Cladosporium sp.

<400> SEQUENCE: 48
tcctccgctt attgatatgc                                               20
```